(12) United States Patent
Seitz et al.

(10) Patent No.: US 6,894,070 B2
(45) Date of Patent: May 17, 2005

(54) 3-AMINOCARBONYL SUBSTITUTED BENZOYLPYRAZOLONES

(75) Inventors: Thomas Seitz, Viernheim (DE); Andreas van Almsick, Karben (DE); Lothar Willms, Hofheim (DE); Thomas Auler, Bad Soden (DE); Hermann Bieringer, Eppstein (DE); Hubert Menne, Hofheim (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 10/634,725

(22) Filed: Aug. 5, 2003

(65) Prior Publication Data

US 2004/0072693 A1 Apr. 15, 2004

(30) Foreign Application Priority Data

Aug. 6, 2002 (DE) .......................... 102 35 945

(51) Int. Cl.⁷ ........................ A01N 43/56; C07D 231/08
(52) U.S. Cl. ..................... 514/407; 548/367.4
(58) Field of Search ........................ 548/367.4; 514/407

(56) References Cited

FOREIGN PATENT DOCUMENTS

| EP | 0 282 944 A2 | 9/1988 |
|---|---|---|
| EP | 0 352 543 | 1/1990 |
| WO | WO-97/41106 | 11/1997 |
| WO | WO-97/46530 | 12/1997 |

OTHER PUBLICATIONS

English language abstract of JP 11292849 (Oct. 26, 1999).

*Primary Examiner*—Kamal A. Saeed
(74) *Attorney, Agent, or Firm*—Connolly Bove Lodge & Hutz LLP

(57) ABSTRACT

A description is given of derivatives of benzoylpyrazoles of the formula (I) and of their use as herbicides.

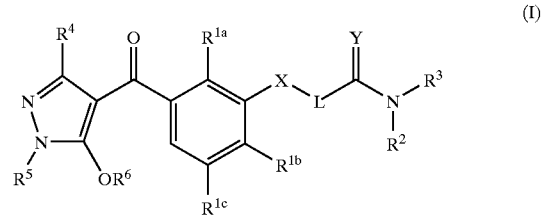

In this formula (I) $R^{1a}$, $R^{1b}$, $R^{1c}$, $R^2$, $R^3$, $R^4$ and $R^5$ stand for various radicals, X for a bridging atom, L for a carbon chain and Y for a chalcogen atom.

13 Claims, No Drawings

3-AMINOCARBONYL SUBSTITUTED BENZOYLPYRAZOLONES

The invention pertains to the technical field of herbicides, particularly that of herbicides from the benzoylpyrazolone class, for selectively controlling broadleaf and gramineous weeds in crops of useful plants, especially in rice crops.

From a variety of publications it is already known that certain benzoylpyrazolones possess herbicidal properties. For instance, EP-A 0 352 543 discloses benzoylpyrazolones whose phenyl ring carries in its position 3 a radical selected inter alia from alkylcarbonyl, aminoalkyl, and alkoxycarbonylalkyl attached via an oxygen atom. WO 97/41106 describes benzoylpyrazolones which carry in the same position, for example, an alkylaminosulfonyl or alkylsulfonylamino radical. The compounds known from these publications, however, frequently exhibit a herbicidal activity which is inadequate.

It is an object of the present invention to provide herbicidally effective compounds having herbicidal properties which are improved over those of the prior art compounds.

It is has now been found that benzoylpyrazolones which carry in position 3 of their phenyl ring an aminocarbonyl alkyl radical attached via an atom from the group consisting of oxygen, nitrogen and sulfur are especially suitable herbicides. The present invention accordingly first provides compounds of the formula (I) or salts thereof

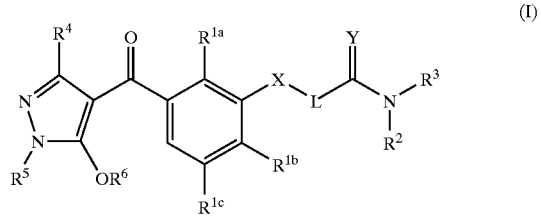

(I)

in which the radical and the indices have the following definitions:

X is O, $S(O)_n$, N—H or N—$R^2$;

L is a straight-chain or branched ($C_1$–$C_6$)-alkylene, ($C_2$–$C_6$)-alkenylene or ($C_2$–$C_6$)alkynylene chain substituted by w radicals from the group consisting of halogen, cyano, and nitro and by v radicals $R^2$;

Y is oxygen or sulfur;

$R^{1a}$, $R^{1b}$, $R^{1c}$ independently are each hydrogen, mercapto, nitro, halogen, cyano, thiocyanato, ($C_1$–$C_6$)-alkyl-CO—O, ($C_1$–$C_6$)-alkyl-$S(O)_n$—O, ($C_1$–$C_6$)-alkyl-$S(O)_m$, ($C_1$–$C_6$)-haloalkyl-$S(O)_m$, ($C_3$–$C_7$)-cycloalkyl-$S(O)_m$, di-($C_1$–$C_6$)-alkyl-N—$SO_2$, ($C_1$–$C_6$)-alkyl-$SO_2$—NH, ($C_1$–$C_6$)-alkyl-NH—CO, di-($C_1$–$C_6$)-alkyl-N—CO, ($C_1$–$C_6$)-alkyl-$SO_2$—[($C_1$–$C_6$)-alkyl] amino, ($C_1$–$C_6$)-alkyl-CO—[($C_1$–$C_6$)-alkyl]amino, ($C_1$–$C_6$)-alkyl-O—$CH_2$, ($C_1$–$C_6$)-alkyl-$S(O)_n$—$CH_2$, ($C_1$–$C_6$)-alkyl-NH—$CH_2$, 1,2,4-triazol-1-yl, 1,2,4-triazol-1-yl-$CH_2$, or are each ($C_1$–$C_6$)-alkyl-$(Y)_p$, ($C_2$–$C_6$)-alkenyl-$(Y)_p$, ($C_2$–$C_6$)-alkynyl-$(Y)_p$, ($C_3$–$C_9$)-cycloalkyl-$(Y)_p$, ($C_3$–$C_9$)-cycloalkenyl-$(Y)_p$, ($C_1$–$C_6$)-alkyl-($C_3$–$C_9$)-cycloalkyl-$(Y)_p$ or ($C_1$–$C_6$)-alkyl-($C_3$–$C_9$)-cycloalkenyl-$(Y)_p$ each of which is substituted by v radicals from the group consisting of cyano, nitro and halogen;

$R^2$, $R^3$ independently are each hydrogen, ($C_1$–$C_6$)-alkyl, ($C_2$–$C_6$)-alkenyl, ($C_2$–$C_6$)-alkynyl, ($C_3$–$C_9$)-cycloalkyl, ($C_3$–$C_9$)-cycloalkenyl, ($C_1$–$C_6$)-alkyl-($C_3$–$C_9$)-cycloalkyl, ($C_1$–$C_6$)-alkyl-($C_3$–$C_9$)-cycloalkenyl, ($C_2$–$C_6$)-alkenyl-($C_3$–$C_9$)-cycloalkyl, ($C_2$–$C_6$)-alkenyl-($C_3$–$C_9$)-cycloalkenyl, ($C_2$–$C_6$)-alkynyl-($C_3$–$C_9$)-cycloalkyl, ($C_2$–$C_6$)-alkynyl-($C_3$–$C_9$)-cycloalkenyl, straight-chain or branched [O—C($R^6$)$_2$]$_w$—[O—C($R^6$)$_2$]$_x$—$R^6$, ($C_1$–$C_6$)-alkyl-aryl, ($C_2$–$C_6$)-alkenyl-aryl, ($C_2$–$C_6$)-alkynyl-aryl, straight-chain or branched [O—C($R^6$)$_2$]$_w$—[O—C($R^6$)$_2$]$_x$-aryl, the last 16 of the abovementioned radicals being substituted by v radicals from the group consisting of cyano, nitro and halogen, or are each aryl, heterocyclyl or heteroaryl each substituted by v radicals consisting of the group of cyano, nitro, halogen, ($C_1$–$C_6$)-alkyl-$(Y)_p$ and halo-($C_1$–$C_6$)-alkyl-$(Y)_p$, or $R^2$ and $R^3$ together with the nitrogen atom linking them form a 5- or 6-membered saturated, partly unsaturated or fully unsaturated ring which contains n heteroatoms from the group consisting of oxygen and nitrogen and is substituted by v radicals from the group consisting of cyano, nitro, halogen, ($C_1$–$C_6$)-alkyl-$(Y)_p$ and halo-($C_1$–$C_6$)-alkyl-$(Y)_p$, or $R^2$ and $R^3$ together with the nitrogen atom linking them form a ring from the group consisting of benzothiazole, benzoxazole, benzopyrazole and benzopyrrole which is substituted by v radicals from the group consisting of cyano, nitro, halogen, ($C_1$–$C_6$)-alkyl$(Y)_p$, and halo-($C_1$–$C_6$)-alkyl-$(Y)_p$;

$R^4$ is hydrogen, ($C_1$–$C_6$)-alkyl or ($C_1$–$C_6$)-haloalkyl, ($C_3$–$C_9$)-cycloalkyl or ($C_3$–$C_9$)-halocycloalkyl;

$R^5$ is ($C_1$–$C_6$)-alkyl, halo-($C_1$–$C_6$)-alkyl, ($C_3$–$C_9$)-cycloalkyl, ($C_3$–$C_9$)-halo-cycloalkyl, or is phenyl substituted by v radicals from the group consisting of halogen, nitro, cyano, ($C_1$–$C_4$)-alkyl, halo-($C_1$–$C_4$)-alkyl, ($C_1$–$C_4$)-alkoxy and halo-($C_1$–$C_4$)-alkoxy;

$R^6$ is hydrogen, ($C_1$–$C_6$)-alkyl, halo-($C_1$–$C_6$)-alkyl, ($C_1$–$C_6$)-alkylcarbonyl, halo-($C_1$–$C_6$)-alkylcarbonyl, ($C_1$–$C_6$)-alkoxycarbonyl, halo-($C_1$–$C_6$)-alkoxycarbonyl, ($C_1$–$C_6$)-alkylaminocarbonyl, halo-($C_1$–$C_6$)-alkylaminocarbonyl, ($C_1$–$C_6$)-dialkylaminocarbonyl, halo-($C_1$–$C_6$)-dialkylaminocarbonyl, ($C_1$–$C_6$)-alkylsulfonyl, halo-($C_1$–$C_6$)-alkylsulfonyl, or is benzyl, benzoyl, benzoylmethyl, phenoxycarbonyl or phenylsulfonyl each of which is substituted by v radicals from the group consisting of halogen, nitro, cyano, ($C_1$–$C_4$)-alkyl, halo-($C_1$–$C_4$)-alkyl, ($C_1$–$C_4$)-alkoxy and halo-($C_1$–$C_4$)-alkoxy;

m is 1 or 2;

n is 0, 1 or 2;

p is 0 or 1;

v is 0, 1, 2 or 3;

w and x independently are each 0,1, 2, 3 or 4;

w and x should not both be zero at the same time.

Where $R^6$ is hydrogen the compounds of the formula (I) according to the invention can occur as different tautomeric structures depending on external conditions, such as solvent and pH. Depending on the nature of the substituents the compounds of the formula (I) contain an acidic proton, which can be removed by reaction with a base. Examples of suitable bases include hydrides, hydroxides, and carbonates of alkali metals and alkaline earth metals, such as lithium, sodium, potassium, magnesium, and calcium, and also ammonia and organic amines such as triethylamine and pyridine. Such salts are likewise provided by the invention.

In formula (I) and all subsequent formulae alkyl radicals having more than two carbon atoms can be straight-chain or branched. Alkyl radicals are for example, methyl, ethyl, n- or i-propyl, n-, i-, t- or 2-butyl, pentyls, hexyls, such as n-hexyl, i-hexyl, and 1,3-dimethylbutyl. The carbon chain L can likewise be straight-chain or branched depending on the number of its carbon atoms. The radicals attached to the chain can be located at any position thereon.

Where a group is multiply substituted by radicals this means that said group is substituted by one or more, identical or different, radicals selected from those specified.

Cycloalkyl is a carbocyclic saturated ring system having three to nine carbon atoms, e.g. cyclopropyl, cyclopentyl or cyclohexyl. Similarly, cycloalkenyl is a monocyclic alkenyl group having three to nine carbon ring members, e.g. cyclopropenyl, cyclobutenyl, cyclopentyl or cyclohexenyl, the double bond being located in any position. In the case of composite radicals, such as cycloalkylalkenyl, the first-mentioned radical may be located at any position on that mentioned second.

In the case of a doubly substituted amino group, such as dialkylamino, these two substituents can be identical or different.

Halogen is fluorine, chlorine, bromine or iodine. Haloalkyl, haloalkenyl and haloalkynyl are alkyl, alkenyl or alkynyl, respectively, substituted fully or partly by halogen, preferably by fluorine, chlorine and/or bromine, in particular by fluorine or chlorine, examples being $CF_3$, $CHF_2$, $CH_2F$, $CF_3CF_2$, $CH_2FCHCl$, $CCl_3$, $CHCl_2$, $CH_2CH_2Cl$; haloalkoxy is for example $OCF_3$, $OCHF_2$, $OCH_2F$, $CF_3CF_2O$, $OCH_2CF_3$ and $OCH_2CH_2Cl$; similar comments apply to haloalkyl and other halogen-substituted radicals.

The term "heterocyclyl" is to be understood as referring to three- to six-membered, saturated or partially unsaturated, monocyclic or polycyclic heterocycles containing from one to three heteroatoms selected from a group consisting of oxygen, nitrogen and sulfur. Linking can take place at any position of the heterocycle, where chemically possible. Examples include oxiranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazoldinyl, 4-isoxazolidinyl, 5-isoxoazolidinyl, 3-isothioazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxa-diazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydro-isoxazol-4-yl, 4,5-dihydroisoxazol-5-yl, 2,3-dihydroisothiazol-3-yl, 2,3-dihydroisothiazol-4-yl, 2,3-dihydroisothiazol-5-yl, 2,5-dihydroisoxazol-3-yl, 2,5-dihydroisoxazol-4-yl, 2,5-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydrooxazol-3-yl, 2,3-dihydrooxazol-4-yl, 2,3-dihydro-oxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 1-morpholinyl, 2-morpholinyl, 3-morpholinyl, 1-piperidinyl, 2-piperidinyl, 3-piperidinyl, 4-piperidinyl, 3-tetrahydropyridazinyl, 4-tetrahydro-pyridazinyl, 2-tetrahydropyrimidinyl, 4-tetrahydropyrimidinyl, 5-tetrahydro-pyrimidinyl, 2-tetrahydropyrazinyl, 1,3,5-tetrahydrotriazin-2-yl, 1,2,4-tetrahydro-triazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,3-dithian-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl.

Aryl is an aromatic monocyclic or polycyclic hydrocarbon radical, e.g. phenyl, naphthyl, biphenyl and phenanthryl, preferably phenyl. Linking may in principle be at any aryl position.

Heteroaryl is an aromatic monocyclic, bicyclic or tricyclic radical containing in addition to carbon ring members from one to four nitrogen atoms or from one to three nitrogen atoms and one oxygen or one sulfur atom or an oxygen or a sulfur atom. Linking can be at any aryl position, where chemically possible. Examples of 5-membered heteroaryl are 2-pyrrolyl, 3-pyrrolyl, 1-pyrazolyl, 3-pyrazolyl, 4-pyrazolyl, 5-pyrazolyl, 2-imidazolyl, 4-imidazolyl, 1,2,4-triazolyl-3-yl, 1,3,4-triazol-2-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-Imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl. Examples of 6-membered heteroaryl are 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl. Examples of fused 5-membered heteroaryl are benzothiazol-2-yl and benzoxazol-2-yl. Examples of benzo-fused 6-membered heteroaryl are quinoline, isoquinoline, quinazoline and quinoxaline.

Where a group is multiply substituted it is implicitly understood that the combination of the different substituents must respect the general principles of the structure of chemical compounds; that is, that no compounds must be formed which are known to the skilled worker to be chemically unstable or impossible.

Depending on the nature and linking of their substituents the compounds of the formula (I) can exist as stereoisomers. Where, for example, there are one or more asymmetric carbon atoms, enantiomers and diastereomers may occur. Stereoisomers can be obtained from the as-prepared mixtures by standard separation methods, e.g., by chromatographic separation techniques. Likewise, stereoisomers may be prepared selectively using stereoselective reactions and optically active starting materials and/or auxiliaries. The invention also relates to all of the stereoisomers and mixtures thereof which, while embraced by the general formula (I), have not been specifically defined.

Compounds of the formula (I) which have found advantageous include those wherein R², R³ independently are each hydrogen, $(C_1-C_6)$-alkyl, $(C_2-C_6)$-alkenyl, $(C_2-C_6)$-alkynyl, $(C_3-C_9)$-cycloalkyl, $(C_3-C_9)$-cycloalkenyl, $(C_1-C_6)$-alkyl-$(C_3-C_9)$-cycloalkyl, $(C_1-C_6)$-alkyl-$(C_3-C_9)$-cycloalkenyl, $(C_2-C_6)$-alkenyl-$(C_3-C_9)$-cycloalkyl, $(C_2-C_6)$-alkenyl-$(C_3-C_9)$-cycloalkenyl, $(C_2-C_6)$-alkynyl-$(C_3-C_9)$-cycloalkyl, $(C_2-C_6)$-alkynyl-$(C_3-C_9)$-cycloalkenyl, straight-chain or branched $[O-C(R^6)_2]_w-[O-C(R^6)-_2]_x-R^6$, $(C_1-C_6)$-alkyl-aryl, $(C_2-C_6)$-alkenyl-aryl, $(C_2-C_6)$-alkynyl-aryl, straight-chain or branched $[O-C(R^6)_2]_w-[O-C(R^6)_2]_x$-aryl, the last 16 of the abovementioned radicals being substituted by the radicals consisting of cyano, nitro, and halogen, aryl substituted by v radicals from the group consisting of cyano, nitro, halogen, $(C_1-C_6)$-alkyl-$(Y)_p$ and halo-$(C_1-C_6)$-alkyl-$(Y)_p$ or R² and R³ together with the nitrogen atom linking them form a 5- or 6-membered saturated, partly unsaturated or fully unsaturated ring which contains n heteroatoms from the group consisting of oxygen and nitrogen and is substituted by v radicals from the group consisting of cyano, nitro, halogen, $(C_1-C_6)$-alkyl-$(Y)_p$ and halo-$(C_1-C_6)$-alkyl-$(Y)_p$, or R² and R³ together with the hydrogen atom linking them form a ring from the group consisting of benzothiazole, benzoxazole, benzopyrazole and benzopyrrole which is substituted by v radicals from the group consisting of cyano, nitro, halogen, $(C_1-C_6)$-alkyl-$(Y)_p$ and halo-$(C_1-C_6)$-alkyl-$(Y)_p$, and the other substituents and indices are each as defined above.

Preference is given to compounds of the general formula (I) wherein Y is oxygen and $R^{1c}$ is hydrogen and the other substituents and indices are each as defined above.

Preference is also given to compounds of the general formula (I) wherein

X is O or $S(O)_n$;

$R^{1a}$, $R^{1b}$ independently are each F, Cl, Br, $CH_3$, $CH_3S$, $CH_3O$, $CH_3SO_2$, $C_2H_5SO_2$, $CF_3CH_2SO_2$, cyclopropyl-$SO_2$, $CF_3$ or $NO_2$;

R², R³ independently are each hydrogen, $(C_1-C_6)$-alkyl, $(C_2-C_6)$-alkenyl, $(C_2-C_6)$-alkynyl, $(C_3-C_9)$-cycloalkyl, $(C_1-C_6)$-alkyl-$(C_3-C_9)$-cycloalkyl, the last 5 radicals being substituted by v radicals from the group consisting of cyano, nitro, and halogen, or are aryl or $(C_1-C_6)$-alkyl-aryl, the last 2 radicals being substituted by v radicals from the group consisting of cyano, nitro, halogen, $(C_1-C_6)$-alkyl-$(Y)_p$ and halo-$(C_1-C_6)$-alkyl-$(Y)_p$, or R² and R³together with the nitrogen atom linking them form a 5- or 6-membered saturated, partly unsaturated or fully unsaturated ring which contains n heteroatoms from the group consisting of oxygen and nitrogen and is substituted by v radicals from the group consisting of cyano, nitro, halogen, $(C_1-C_6)$-alkyl-$(Y)_p$ and halo-$(C_1-C_6)$-alkyl-$(Y)_p$, or R² and R³ together with the nitrogen atom linking them form a ring from the group consisting of benzothiazole, benzoxazole, benzopyrazole and benzopyrrole which is substituted by v radicals from the group consisting of cyano, nitro, halogen, $(C_1-C_6)$-alkyl-$(Y)_p$ and halo $(C_1-C_6)$-alkyl-$(Y)_p$, and the other substituents and indices are each as defined above.

Particular preference is given to compounds of general formula (I) wherein X is oxygen and the other substituents and indices are each as defined above.

Likewise preferred are compounds of the general formula (I) wherein

R², R³ independently are each hydrogen or $(C_1-C_6)$-alkyl, or R² and R³ together with the nitrogen atom linking them form a ring from the group consisting of morpholine, pyrrolidine, piperidine, pyrrol, pyrazole and 2,3-dihydroindol;

R⁴ is hydrogen, methyl or cyclopropyl, and the other substituents and indices are each as defined above.

Particular preference is also given to compounds of the general formula (I) wherein R⁶ is hydrogen, $(C_1-C_6)$-alkyl, $(C_1-C_6)$-alkylcarbonyl, $(C_1-C_6)$-alkylsulfonyl, or is benzoyl or phenylsulfonyl each of which is substituted by v radicals from the group consisting of halogen, nitro, cyano, $(C_1-C_4)$-alkyl, halo$(C_1-C_4)$-alkyl, $(C_1-C_4)$-alkoxy and halo$(C_1-C_4)$-alkoxy, and the other substituents and indices are each as defined above.

Special preference is given to compounds of the general formula (I) wherein

L is $CH_2$, $C(CH_3)H$ or $CH_2CH_2$;

$R^{1a}$, $R^{1b}$ independently are each Cl, Br, $NO_2$, $CH_3$, $CH_3SO_2$ or $C_2H_5SO_2$;

R², R³ are each hydrogen or $(C_1-C_6)$-alkyl;

R⁵ is methyl or ethyl;

and the other substituents and indices are each as defined above.

In all formulae below the substituents and symbols have the same definition as described in the formula (I) unless otherwise defined.

Compounds of the invention in which R⁶ is hydrogen can be prepared, for example, by the method indicated in scheme 1, by base-catalyzed reaction of a compound of the formula (IIIa) where T is halogen, hydroxyl or alkoxy with a pyrozole (II) in the presence of a cyanide source. Such methods are described for example in WO 99/10328.

Scheme 1:

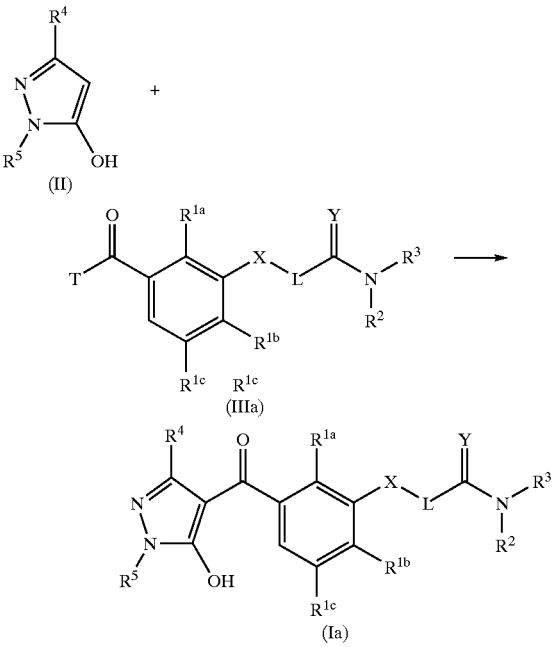

Compounds of the formula (IIIa) can be prepared for example by scheme 2 from compounds of the formula (IIIb)

and (IVa) in which E is a leaving group such as halogen, mesyl, tosyl or triflate in accordance with methods which are known per se. Such methods are known for example from Houben-Weyl Volume 6/3, pp. 54 to 69, Volume 9, pp. 103 to 115 and Volume 11, p. 97.

Scheme 2:

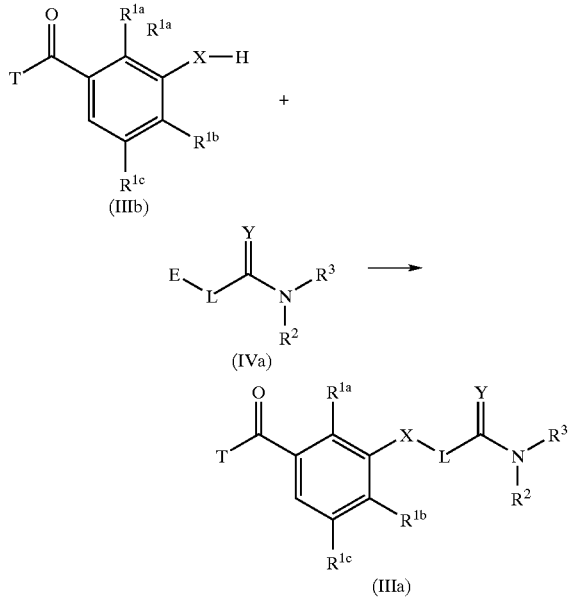

Compounds of the formula (IIIa) can be prepared in accordance with scheme 3 also be reacting compounds of the formula (IIIc) in which $E^1$ is a leaving group such as triflate or nonaflate with compounds of the formula (IVb). Such methods are known for example from WO 98/42648, Houben-Weyl Volume 6/3, pp. 75 to 78, Volume 9, pp. 103 to 105.

Scheme 3:

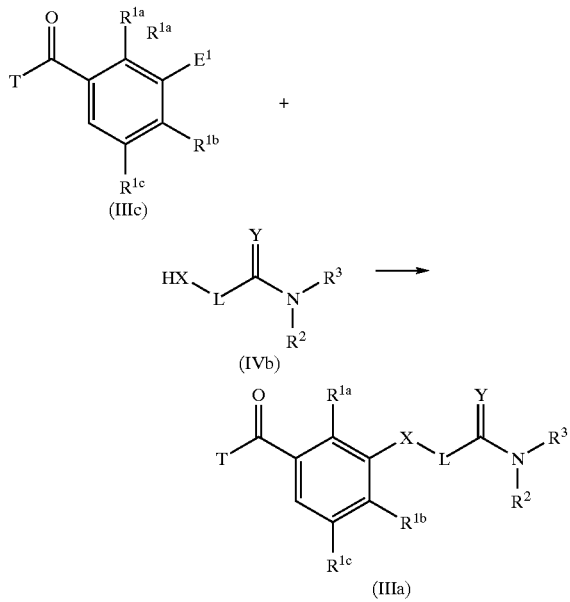

It is likewise possible to prepare compounds of the formula (IIIa) in accordance with scheme 4 also by reacting compounds of the formula (IIId) with compounds $E^2$-$R^3$, in which $E^2$ is a leaving group such as chlorine, bromine or mesyl. Such methods are known for example from Houben-Weyl Volume 8, p. 708, E 5/2, pp. 998 and 1213.

Scheme 4:

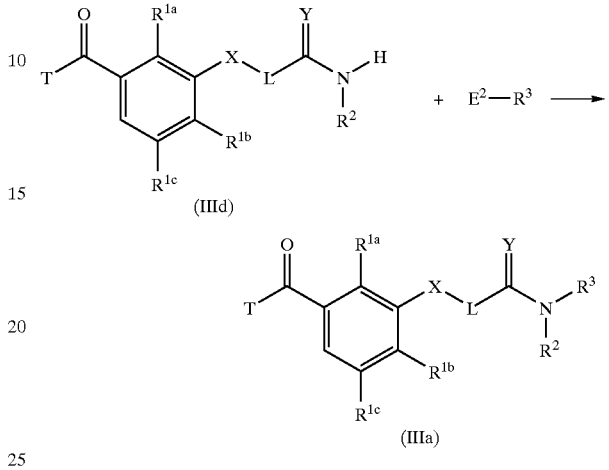

Compounds of the formula (IVa) can be prepared for example by scheme 5 from compounds of the formula (VII) in which E is a group such as chlorine or alkoxy and $E^2$ is a group such as chlorine, bromine, mesyl or tosyl with amines of the formula (VIII) in accordance with methods known per se. Such methods are known for example from Houben-Weyl Volume 8, pp. 647 to 660, Volume 11/2, pp. 1 to 73 (especially pp. 10 to 14 and 20 to 23), Volume E 5/2, pp. 934 to 1135 and from J. Org. Chem. 39 (1974) pp. 2607 to 2612.

Scheme 5:

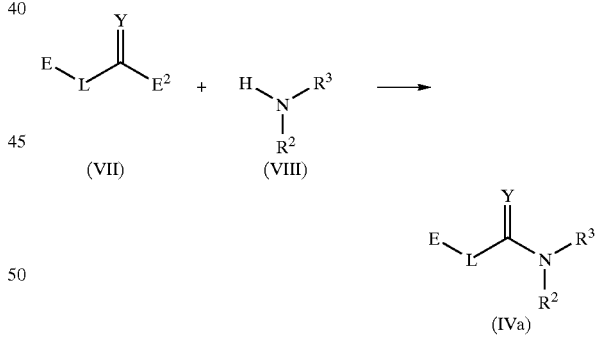

Compounds of the formula (IVb) can be prepared for example by the methods described in U.S. Pat. No. 4,264, 520, DE 3 222 229 and J. Med. Chem. 39 (1996) 26, pp. 5236 to 5245.

Compounds of the formula (I) according to the invention in which $R^6$ stands for radicals other than hydroxyl can be prepared for example in accordance with scheme 6 by substitution reactions which are known per se to the skilled worker. For that purpose compounds of the formula (Ia) are reacted with compounds of the formula (VIII), in which $E^3$ is a nucleophillically substitutable leaving group. Such methods are known for example from WO 99/10328.

Scheme 6:

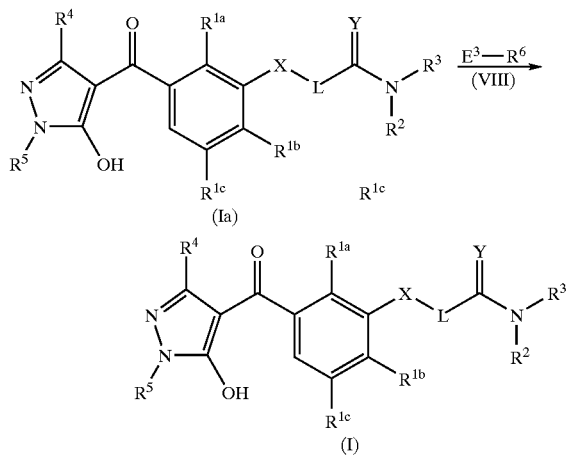

The compounds of the formula (I) according to the invention have an excellent herbicidal activity against a broad range of economically important monocotyledonous and dicotyledonous weed plants. The active substances control perennial weeds equally well which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the perennial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennials. Harmful plants which are found under the specific culture conditions of rice, such as, for example, *Echinochloa, Sagittaria, Alisma, Eleocharis, Scirpus* and *Cyperus* are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that competition by the weeds, which is detrimental for the crop plants, is thus eliminated at a very early stage and in a sustained manner. In particular, the compounds according to the invention have an outstanding action against *Amaranthus retroflexus, Avena* sp., *Echinochloa* sp., *Cyperus serotinus, Lolium multiflorum, Setaria viridis, Sagittaria pygmaea, Scirpus juncoides, Sinapis* sp. and *Stellaria media*.

Although the compounds according to the invention have an outstanding herbicidal activity against monocotyledonous and dicotyledonous weeds, crop plants of economically important crops such as, for example, wheat, barley, rye, rice, maize, sugar beet, cotton and soya, only suffer negligible damage, if any. In particular, they are outstandingly well tolerated in wheat, maize and rice. This is why the present compounds are highly suitable for the selective control of undesired vegetation in stands of agricultural useful plants or of ornamentals.

Owing to their herbicidal properties, the active substances can also be employed for controlling harmful plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased starch content or whose starch quality has been modified, or those whose fatty acid spectrum in the harvested material is different.

The compounds of the formula (I) according to the invention or their salts are preferably employed in economically important transgenic crops of useful plants and ornamentals, for example cereals such as wheat, barley, rye, oats, millet, rice, cassava and maize, or else crops of sugar beet, cotton, soya, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

recombinant modifications of crop plants for the purposes of modifying the starch synthesized in the plants (for example WO 92/11376, WO 92/14827, WO 91/19806), transgenic crop plants which exhibit resistances to certain herbicides of the glufosinate type (cf. eg. EP-A-0242236, EP-A-242246), glyphosate type (WO 92/00377) or of the sulfonylurea type (EP-A-0257993, U.S. Pat. No. 5,013,659)

transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid spectrum (WO 91/13972), A large number of techniques in molecular biology, with the aid of which novel transgenic plants with modified properties can be generated, are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423–431.

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or the expression of at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give intact plants. In principle, the transgenic plants can be plants of any desired plant species, i.e. both monocotyledonous and dicotyledonous plants.

Thus, transgenic plants can be obtained which exhibit modified properties owing to the overexpression, suppression or inhibition of homologous (i.e. natural) genes or gene sequences or expression of heterologous (i.e. foreign) genes or gene sequences.

When using the active substances according to the invention in transgenic crops, effects are frequently observed in addition to the effects against harmful plants to be observed in other crops, which are specific for the application in the transgenic crop in question, for example a modified or specifically widened weed spectrum which can be controlled, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling harmful plants in transgenic crop plants.

The substances according to the invention additionally have outstanding growth-regulatory properties in crop plants. They engage in the plants' metabolism in a regulatory fashion and can thus be employed for the targeted control of plant constituents and for facilitating harvesting, such as, for example, triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops, allowing lodging to be reduced or prevented completely.

The compounds according to the invention can be employed in the form of wettable powders, emulsifiable concentrates, sprayable solutions, dusts or granules in the customary preparations. The invention therefore furthermore relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, such as butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water based or oil based. They can be prepared for example by wet-grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the tackifiers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441–445 (1986) or "The Pesticide Manual", 11th edition, The British Crop Protection Council and the Royal Soc. of Chemistry, 1997 and literature cited therein. Known herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number):

acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuronmethyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyidithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentylester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; mesotrione; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy] propanoic acid and its methyl ester; suclotrione; sulfentrazon (FMC-97285, F-6285); sulfazuron; sulfometuronmethyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations, which are present in commercially available form, are diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use. The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

The starting compound ethyl 2,4-dibromo-3-hydroxybenzoate was prepared as described in U.S. Pat. No. 5,026,896.

The abbreviation RT stands for room temperature. $R^f$ is the retention value.

Preparation of 1-methyl-4-(2-chloro-3-(pyrrolidinocarbonylmethoxy)4-ethylsulfonylbenzoyl) pyrazolone (tabular example No. 1.60)

Step 1: Methyl 2-chloro-3-hydroxy-4-ethylsulfonylbenzoate 33.0 g of 2-chloro-3-hydroxy-4-ethylsulfonylbenzoic acid is dissolved in 1300 ml of MeOH. 174 ml of conc. $H_2SO_4$ were added dropwise and the mixture was then heated under reflux for 5 hours. The mixture was concentrated and the residue was taken up in $CH_2Cl_2$. It was washed with water, dried over $Na_2SO_4$ and fully concentrated. This gave methyl 2-chloro-3-hydroxy-4-ethylsulfonylbenzoate as a viscous yellow oil.

Yield: 28.23 g (81% of theory) $R^f$: (ethyl acetate) 0.45 $^1$H NMR: δ[$CDCl_3$] 1.32 (t, 3H), 3.24 (q, 2H), 3.96 (s, 3H), 7.38 (d, 1H), 7.65 (d, 1H)

Step 2: Methyl 2-chloro-3-(pyrrolidinocarbonylmethoxy)-4-ethylsulfonylbenzoate 0.595 g of $K_2CO_3$, 0.107 g of KI and 0.459 g of chloroacetyl pyrrolidide were introduced in 30 ml of acetone. At RT 0.600 g of methyl 2-chloro-3-hydroxy-4-ethylsulfonylbenzoate were added and the mixture was heated at reflux for 4 hours. It was then poured into water and extracted with ethyl acetate. The organic phases were washed with water, dried over $Na_2SO_4$ and concentrated. Chromatography on silica gel (eluent: n-heptane/ethyl acetate) gave methyl 2-chloro-3-(pyrrolidinocarbonylmethoxy)-4-ethylsulfonylbenzoate as a viscous colorless oil.

Yield: 0.50 g (58% of theory) $^1$H NMR: δ[$CDCl_3$] 1.24 (t, 3H), 1.88 (m, 2H), 2.00 (m, 2H), 3.29 (m, 2H), 3.57 (m, 4H), 3.69 (q, 2H), 4.00 (s, 3H), 4.82 (s, 2H), 7.69 (d, 1H), 7.93 (d, 1H).

Step 3: 2-Chloro-3-(pyrrolidinocarbonylmethoxy)-4-ethylsulfonylbenzoic acid 0.500 g of methyl 2-chloro-3-(pyrrolidinocarbonylmethoxy)-4-ethylsulfonylbenzoate were dissolved in 20 ml of THF and 20 ml of water, 0.056 g of NaOH was added and the mixture was stirred at RT for 12 hours. The mixture was admixed with 6 N HCl and extracted with $CH_2Cl_2$. Drying of the organic phase over $Na_2SO_4$ gave 2-chloro-3-(pyrrolidinocarbonylmethoxy)-4-ethylsulfonylbenzoic acid as a viscous colorless oil.

Yield: 0.42 g (87% of theory) $^1$H NMR: δ[$CDCl_3$] 1.22 (t, 3H), 1.91 (m, 2H), 2.00 (m, 2H), 3.32 (m, 2H), 3.60 (m, 4H), 4.85 (s, 2H), 7.77 (d, 1H), 7.91 (d, 1H).

Step 4: 5-(1-Methyl-pyrazolyl)(2-chloro-3-(pyrrolidinocarbonylmethoxy)-4-ethylsulfonyl)-benzoate 0.210 g (0.60 mmol) of 2-chloro-3-(pyrrolidinocarbonylmethoxy)4-ethylsulfonylbenzoic acid, 0.092 g of 1-methylpyrazolone, 0.109 g of N'-(3-dimethylaminopropyl)-N-ethylcarbodiimide hydrochloride and 0.001 g of DMAP were stirred in 15 ml of $CH_2Cl_2$ at RT for 3 hours. The mixture was then acidified with 0.5 N HCl and the phases were separated. The aqueous phase was extracted with $CH_2Cl_2$. Drying of the organic phases over $Na_2SO_4$ and concentration gave 5-(1-methylpyrazolyl)(2-chloro-3-(pyrrolidinocarbonylmethoxy)-4-ethylsulfonyl) benzoate in the form of brown resin which was sufficiently pure for subsequent reaction.

Yield: 0.210 g $^1$H NMR: δ[$CDCl_3$] 1.26 (t, 3H), 1.89 (m, 2H), 2.00 (m, 2H), 3.28 (m, 2H), 3.58 (m, 2H), 3.66 (q, 2H), 3.75 (s, 3H), 4.83 (s, 2H), 6.15 (s, 1H), 7.41 (s, 1H), 7.79 (d, 1H), 7.96 (d, 1H).

Step 5: 1-Methyl-4-(2-chloro-3-(pyrrolidinocarbonylmethoxy)-4-ethylsulfonylbenzoyl) pyrazolone 0.210 g of 5-(1-Methylpyrazolyl)(2-chloro-3-(pyrrolidinocarbonylmethoxy)-4-ethylsulfonyl)benzoate was dissolved in 10 ml of acetonitrile. 3 drops of acetone cyanohydrin, 0.079 g of $NEt_3$ and 0.009 g of KCN were added. After stirring at RT for 3 hours the mixture was diluted with water, acidified with 0.5 N HCl and extracted with $CH_2Cl_2$. Drying over $Na_2SO_4$, concentration and chromatography on reversed-phase silica gel (eluent: acetonitrile/water gradient) gave 1-methyl-4-(2-chloro-3-(pyrrolidinocarbonylmethoxy)4-ethylsulfonylbenzoyl)pyrazolone as a viscous colorless oil.

Yield: 0.036 g (about 11% of theory) $R^f$ (ethyl acetate): 0.01 $^1$H NMR: δ[$CDCl_3$] 1.28 (t, 3H), 1.91 (m, 2H), 2.00 (m, 2H), 3.31 (m, 2H), 3.59 (m, 2H), 3.69 (q, 2H), 3.73 (s, 3H), 4.85 (s, 2H), 7.35 (s, 1H), 7.41 (d, 1H), 8.00 (d, 1H).

Preparation of 1,3-dimethyl-4-(2,4-dibromo-3-(N,N-di-n-propylaminocarbonylmethoxy)benzoyl)pyrazolone (tabular example no. 3.34)

Step 1: Ethyl 2,4-dibromo-3-(N,N-di-n-propylaminocarbonylmethoxy)benzoate 0.853 g of $K_2CO_3$, 0.154 g of KI and 1.000 g of ethyl 2,4-dibromo-3-hydroxybenzoate were introduced in 10 ml of acetone. At RT 0.783 g of N,N-di-n-propylchloroacetamide was added. The mixture was then heated at reflux for 4 hours. It was subsequently poured into water and extracted with diisopropyl ether. The organic phases were washed with water, dried over $Na_2SO_4$ and concentrated. Chromatography on silica gel (eluent: n-heptane/ethyl acetate) gave ethyl 2,4-dibromo-3-(N,N-di-n-propylaminocarbonylmethoxy)benzoate as brown oil.

Yield: 1.27 g (83% of theory) $^1$H NMR: δ[$CDCl_3$] 0.93 (m, 6H), 1.20 (t, 3H), 1.64 (m, 4H), 3.32 (m, 4H), 4.20 (q, 4H), 4.66 (s, 2H), 7.40 (d, 1H), 7.57 (d, 1H).

Step 2: 2,4-Dibromo-3-(N,N-di-n-propylaminocarbonylmethoxy)benzoic acid 1.24 g (2.70 mmol) of ethyl 2,4-dibromo-3-(N,N-di-n-propylaminocarbonylmethoxy)benzoate were dissolved in 10 ml of THF and 10 ml of $H_2O$, and 0.117 g of NaOH was added. After stirring at RT for 12 h the mixture was admixed with 6 N HCl and extracted with $CH_2Cl_2$. Drying of the organic phase over $Na_2SO_4$ gave 2,4-dibromo-3-(N,N-di-n-propylaminocarbonylmethoxy)benzoic acid as a viscous colorless oil.

Yield: 1.05 g (81% of theory) $^1$H NMR: δ[$CDCl_3$] 0.90 (m, 6H), 1.62 (m, 4H), 3.37 (m, 4H), 3.72 (s, 3H), 4.72 (s, 2H), 7.39 (d, 1H), 7.59 (d, 1H).

Step 3: 5-(1,3-Dimethylpyrazolyl)(2,4-dibromo-3-(N,N-di-n-propylaminocarbonylmethoxy)benzoate 0.510 g of 2,4-dibromo-3-(N,N-di-n-propylaminocarbonylmethoxy)benzoic acid, 0.144 g of 1,3-dimethylpyrazolone, 0.228 g of N'-(3-dimethylaminopropyl)-N-ethylcarbodiimide hydrochloride and 0.001 g of DMAP were stirred in 15 ml of $CH_2Cl_2$ at RT for 2 hours. The mixture was subsequently diluted with 50 ml of water and stirred vigorously for 30 minutes. Following acidification with 0.5 N HCl the phases were separated. The aqueous phase was extracted with $CH_2Cl_2$. Drying of the organic phases over $Na_2SO_4$ and concentration gave (5-(1,3-dimethylpyrazolyl))(2,4-dibromo-3-(N,N-di-n-propylaminocarbonylmethoxy)benzoate as a yellow resin which was sufficiently pure for subsequent reaction.

Yield: 0.440 g $^1$H NMR: δ[$CDCl_3$] 0.91 (m, 6H), 1.61 (m, 4H), 2.25 (s, 3H), 3.35 (m, 4H), 3.72 (s, 3H), 4.69 (s, 2H), 6.08 (s, 1H), 7.60 (d, 1H), 7.68 (d, 1H).

Step 4: (1,3-Dimethyl-4-(2,4-dibromo-3-(N,N-di-n-propylaminocarbonylmethoxy)benzoyl)pyrazolone 0.440 g of 5-(1,3-dimethylpyrazolyl)(2,4-dibromo-3-(N,N-di-n-propylaminocarbonylmethoxy)benzoate was dissolved in 10 ml of acetonitrile. 3 drops of acetone cyanohydrin and 0.142 g of $NEt_3$ were added. The mixture was stirred at RT for 1 hour, and then 0.17 g of KCN was added. After a further 3 hours at RT the mixture was concentrated completely and the residue was taken up in water and acidified with 0.5 N HCl. The system was subsequently extracted with $CH_2Cl_2$. Drying of the organic phases over $Na_2SO_4$, concentration and chromatography on reversed-phase silica gel (eluent: acetonitrile/water gradient) gave (1,3-dimethyl-4-(2,4-dibromo-3-(N,N-di-n-propylaminocarbonylmethoxy)benzoyl)pyrazolone as a viscous colorless oil.

Yield: 0.205 g (about 44% of theory) $R^f$ (ethyl acetate): 0.03 $^1$H NMR: δ[$CDCl_3$] 0.92 (m, 6H), 1.63 (m, 4H), 2.16 (s, 3H), 3.32 (m, 4H), 3.64 (s, 3H), 4.71 (s, 2H), 6.94 (d, 1H), 7.65 (d, 1H).

The examples listed in the tables below were prepared in analogy to methods specified above or are obtainable in analogy to the methods specified above.

The abbreviations used here have the following definitions:

| | | | |
|---|---|---|---|
| c = cyclo | i = iso | Bu = butyl | Bz = benzyl |
| Et = ethyl | Me = methyl | Ph = phenyl | Pr = propyl |
| EE = ethyl ethanoate | m.p. = melting point | | |

TABLE 1

Compounds of the general formula (I) according to the invention in which the substituents and symbols are defined as follows:

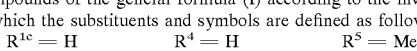

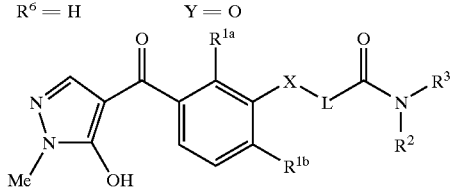

| No. | $R^{1a}$ | $R^{1b}$ | X—L | $NR^2R^3$ | Physical data |
|---|---|---|---|---|---|
| 1.1 | Cl | Cl | $OCH_2$ | $NH_2$ | |
| 1.2 | Br | Br | $OCH_2$ | $NH_2$ | |
| 1.3 | Me | Br | $OCH_2$ | $NH_2$ | |
| 1.4 | Cl | $SO_2Me$ | $OCH_2$ | $NH_2$ | |
| 1.5 | Cl | $SO_2Et$ | $OCH_2$ | $NH_2$ | |
| 1.6 | Me | $SO_2Me$ | $OCH_2$ | $NH_2$ | |
| 1.6a | Me | Cl | $OCH_2$ | NHMe | |

TABLE 1-continued

| No. | | | | | Rf(EE) |
|---|---|---|---|---|---|
| 1.6b | Me | Br | OCH₂ | NHMe | Rf(EE): 0.07 |
| 1.7 | Cl | Cl | OCH₂ | NHEt | |
| 1.8 | Cl | SO₂Me | OCH₂ | NHEt | |
| 1.8a | Me | Cl | OCH₂ | NHEt | |
| 1.8b | Me | Br | OCH₂ | NHEt | Rf(EE): 0.36 |
| 1.9 | Me | SO₂Me | OCH₂ | NHEt | |
| 1.9a | Me | Cl | OCH₂ | NH(Allyl) | |
| 1.9b | Me | Br | OCH₂ | NH(Allyl) | Rf(EE): 0.11 |
| 1.10 | Br | Br | OCH₂ | NH(i-Pr) | |
| 1.11 | Me | Br | OCH₂ | NH(i-Pr) | |
| 1.12 | Me | NO₂ | OCH₂ | NH(i-Pr) | |
| 1.13 | Cl | SO₂Et | OCH₂ | NH(i-Pr) | |
| 1.14 | Cl | Cl | OCH₂ | NH(c-Pr) | |
| 1.15 | Cl | Br | OCH₂ | NH(c-Pr) | |
| 1.15a | Me | Cl | OCH₂ | NH(c-Pr) | |
| 1.16 | Me | Br | OCH₂ | NH(c-Pr) | Rf(EE): 0.15 |
| 1.17 | Me | NO₂ | OCH₂ | NH(c-Pr) | |
| 1.18 | Cl | SO₂Me | OCH₂ | NH(c-Pr) | |
| 1.19 | Cl | Cl | OCH₂ | NMe₂ | Rf(EE): 0.02 |
| 1.20 | Br | Br | OCH₂ | NMe₂ | Rf(EE): 0.01 |
| 1.20a | Me | Cl | OCH₂ | NMe₂ | Rf(EE): 0.02 |
| 1.21 | Cl | Br | OCH₂ | NMe₂ | |
| 1.22 | Me | Br | OCH₂ | NMe₂ | Rf(EE): 0.01 |
| 1.23 | Cl | SO₂Me | | | |
| 1.24 | Me | SO₂Me | | | |
| 1.25 | Cl | SO₂Et | | | |
| 1.26 | Cl | Cl | OCH₂ | NEt₂ | |
| 1.27 | Br | Br | NEt₂ | Rf(EE): 0.01 | |
| 1.27a | Me | Cl | NEt₂ | Rf(EE): 0.02 | |
| 1.28 | Cl | Br | NEt₂ | | |
| 1.29 | Me | Br | NEt₂ | Rf(EE): 0.03 | |
| 1.30 | Cl | SO₂Me | NEt₂ | | |
| 1.31 | Me | SO₂Me | NEt₂ | | |
| 1.32 | Cl | SO₂Et | OCH₂ | NEt₂ | |
| 1.33 | Cl | Cl | OCH₂ | N(n-Pr)₂ | Rf(EE): 0.02 |
| 1.34 | Br | Br | OCH₂ | N(n-Pr)₂ | Rf(EE): 0.03 |
| 1.35 | Cl | Br | OCH₂ | N(n-Pr)₂ | |
| 1.36 | Me | Br | OCH₂ | N(n-Pr)₂ | |
| 1.37 | Cl | SO₂Me | OCH₂ | N(n-Pr)₂ | |
| 1.38 | Me | SO₂Me | OCH₂ | N(n-Pr)₂ | |
| 1.39 | Cl | SO₂Et | OCH₂ | N(n-Pr)₂ | Rf(EE): 0.06 |
| 1.40 | Cl | Cl | OCH₂ | N(i-Pr)₂ | Rf(EE): 0.03 |
| 1.41 | Me | Br | OCH₂ | N(i-Pr)₂ | |
| 1.42 | Me | NO₂ | OCH₂ | N(i-Pr)₂ | |
| 1.43 | NO₂ | Cl | OCH₂ | N(i-Pr)₂ | |
| 1.44 | NO₂ | Br | OCH₂ | N(i-Pr)₂ | |
| 1.45 | Me | SO₂Me | OCH₂ | | |
| 1.46 | Cl | SO₂Et | OCH₂ | N(i-Pr)₂ | Rf(EE): 0.02 |
| 1.47 | Cl | Cl | OCH₂ | NmePh | Rf(EE): 0.07 |
| 1.48 | Me | Br | OCH₂ | NmePh | |
| 1.49 | Me | NO₂ | OCH₂ | NmePh | |
| 1.50 | NO₂ | Cl | OCH₂ | NmePh | |
| 1.51 | NO₂ | Br | OCH₂ | NmePh | |
| 1.52 | Me | SO₂Me | OCH₂ | NmePh | |
| 1.53 | Cl | SO₂Et | OCH₂ | NmePh | Rf(EE): 0.01 |
| 1.54 | Cl | Cl | OCH₂ | —N(pyrrolidinyl) | Rf(EE): 0.02 |
| 1.55 | Br | Br | OCH₂ | —N(pyrrolidinyl) | |
| 1.56 | Cl | Br | OCH₂ | —N(pyrrolidinyl) | |
| 1.57 | Me | Br | OCH₂ | —N(pyrrolidinyl) | |
| 1.58 | Cl | SO₂Me | OCH₂ | —N(pyrrolidinyl) | Rf(EE): 0.02 |
| 1.59 | Me | SO₂Me | OCH₂ | —N(pyrrolidinyl) | |
| 1.60 | Cl | SO₂Et | OCH₂ | —N(pyrrolidinyl) | Rf(EE): 0.01 |
| 1.61 | Cl | Cl | OCH₂ | —N(indolinyl) | Rf(EE): 0.04 |
| 1.62 | Br | Br | OCH₂ | —N(indolinyl) | |
| 1.63 | Cl | Br | OCH₂ | —N(indolinyl) | |
| 1.64 | Me | Br | OCH₂ | —N(indolinyl) | |
| 1.65 | Cl | SO₂Me | OCH₂ | —N(indolinyl) | Rf(EE): 0.04 |
| 1.66 | Me | SO₂Me | OCH₂ | —N(indolinyl) | |
| 1.67 | Cl | SO₂Et | OCH₂ | —N(indolinyl) | |
| 1.68 | Cl | Cl | OCH₂ | —N(morpholinyl) | |

TABLE 1-continued

| | | | | |
|---|---|---|---|---|
| 1.69 | Me | Br | OCH₂ | 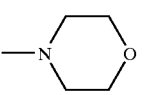 |
| 1.70 | Me | NO₂ | OCH₂ | 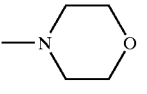 |
| 1.71 | NO₂ | Cl | OCH₂ | 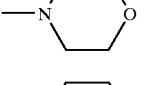 |
| 1.72 | NO₂ | Br | OCH₂ | 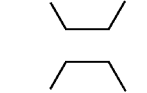 |
| 1.73 | Me | SO₂Me | OCH₂ | 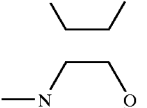 |
| 1.74 | Cl | SO₂Et | OCH₂ | 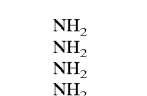 |
| 1.75 | Cl | Cl | OC(Me)H | NH₂ |
| 1.76 | Br | Br | OCH(Me) | NH₂ |
| 1.77 | Me | Br | OCH(Me) | NH₂ |
| 1.78 | Cl | SO₂Me | OCH(Me) | NH₂ |
| 1.79 | Cl | SO₂Et | OCH(Me) | NH₂ |
| 1.80 | Me | SO₂Me | OCH(Me) | NH₂ |
| 1.80a | Cl | Cl | OCH(Me) | NHMe |
| 1.80b | Cl | SO₂Me | OCH(Me) | NHMe |
| 1.80c | Me | Cl | OCH(Me) | NHMe |
| 1.80d | Me | Br | OCH(Me) | NHMe |
| 1.80e | Me | SO₂Me | OCH(Me) | NHMe |
| 1.81 | Cl | Cl | OCH(Me) | NHEt |
| 1.82 | Cl | SO₂Me | OCH(Me) | NHEt |
| 1.82a | Me | Cl | OCH(Me) | NHEt |
| 1.82b | Me | Br | OCH(Me) | NHEt | R^f(EE): 0.05 |
| 1.82c | Cl | Cl | OCH(Me) | NH(Allyl) | R^f(EE): 0.05 |
| 1.82d | Cl | SO₂Me | OCH(Me) | NH(Allyl) |
| 1.82e | Me | Cl | OCH(Me) | NH(Allyl) |
| 1.82f | Me | Br | OCH(Me) | NH(Allyl) |
| 1.82g | Me | SO₂Me | OCH(Me) | NH(Allyl) | R^f(EE): 0.24 |
| 1.83 | Me | SO₂Me | OCH(Me) | NHEt |
| 1.84 | Br | Br | OCH(Me) | NH(i-Pr) |
| 1.85 | Me | Br | OCH(Me) | NH(i-Pr) |
| 1.86 | Me | NO₂ | OCH(Me) | NH(i-Pr) |
| 1.87 | Cl | SO₂Et | OCH(Me) | NH(i-Pr) |
| 1.88 | Cl | Cl | OCH(Me) | NH(c-Pr) | R^f(EE): 0.03 |
| 1.89 | Cl | Br | OCH(Me) | NH(c-Pr) |
| 1.90 | Me | Br | OCH(Me) | NH(c-Pr) |
| 1.91 | Me | NO₂ | OCH(Me) | NH(c-Pr) |
| 1.92 | Cl | SO₂Me | OCH(Me) | NH(c-Pr) |
| 1.93 | Cl | Cl | OCH(Me) | NMe₂ |
| 1.94 | Br | Br | OCH(Me) | NMe₂ |
| 1.95 | Cl | Br | OCH(Me) | NMe₂ |
| 1.96 | Me | Br | OCH(Me) | NMe₂ | R^f(EE): 0.03 |
| 1.97 | Cl | SO₂Me | OCH(Me) | NMe₂ |
| 1.98 | Me | SO₂Me | OCH(Me) | NMe₂ |
| 1.99 | Cl | SO₂Et | OCH(Me) | NMe₂ |
| 1.100 | Cl | Cl | OCH(Me) | NEt₂ |
| 1.101 | Br | Br | OCH(Me) | NEt₂ |
| 1.102 | Cl | Br | OCH(Me) | NEt₂ |
| 1.103 | Me | Br | OCH(Me) | NEt₂ |
| 1.104 | Cl | SO₂Me | OCH(Me) | NEt₂ |
| 1.105 | Me | SO₂Me | OCH(Me) | NEt₂ |
| 1.106 | Cl | SO₂Et | OCH(Me) | NEt₂ |
| 1.107 | Cl | Cl | OCH(Me) | N(n-Pr)₂ |
| 1.108 | Br | Br | OCH(Me) | N(n-Pr)₂ |
| 1.109 | Cl | Br | OCH(Me) | N(n-Pr)₂ |
| 1.110 | Me | Br | OCH(Me) | N(n-Pr)₂ |
| 1.111 | Cl | SO₂Me | OCH(Me) | N(n-Pr)₂ |
| 1.112 | Me | SO₂Me | OCH(Me) | N(n-Pr)₂ |
| 1.113 | Cl | SO₂Et | OCH(Me) | N(n-Pr)₂ |
| 1.114 | Cl | Cl | OCH(Me) | N(i-Pr)₂ |
| 1.115 | Me | Br | OCH(Me) | N(i-Pr)₂ |
| 1.116 | Me | NO₂ | OCH(Me) | N(i-Pr)₂ |
| 1.117 | NO₂ | Cl | OCH(Me) | N(i-Pr)₂ |
| 1.118 | NO₂ | Br | OCH(Me) | N(i-Pr)₂ |
| 1.119 | Me | SO₂Me | OCH(Me) | N(i-Pr)₂ |
| 1.120 | Cl | SO₂Et | OCH(Me) | N(i-Pr)₂ |
| 1.121 | Cl | Cl | OCH(Me) | NmePh |
| 1.122 | Me | Br | OCH(Me) | NmePh |
| 1.123 | Me | NO₂ | OCH(Me) | NmePh |
| 1.124 | NO₂ | Cl | OCH(Me) | NmePh |
| 1.125 | NO₂ | Br | OCH(Me) | NmePh |
| 1.126 | Me | SO₂Me | OCH(Me) | NmePh |
| 1.127 | Cl | SO₂Et | OCH(Me) | NmePh |
| 1.128 | Cl | Cl | OCH(Me) | 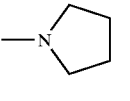 |
| 1.129 | Br | Br | OCH(Me) | 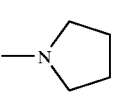 |
| 1.130 | Cl | Br | OCH(Me) |  |
| 1.131 | Me | Br | OCH(Me) | 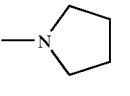 |
| 1.132 | Cl | SO₂Me | OCH(Me) | 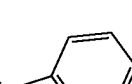 |
| 1.133 | Me | SO₂Me | OCH(Me) | 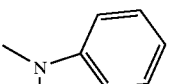 |
| 1.134 | Cl | SO₂Et | OCH(Me) | 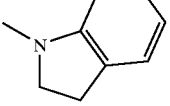 |
| 1.135 | Cl | Cl | OCH(Me) |  |
| 1.136 | Br | Br | OCH(Me) |  |
| 1.137 | Cl | Br | OCH(Me) |  |

TABLE 1-continued

| | | | | |
|---|---|---|---|---|
| 1.138 | Me | Br | OCH(Me) | 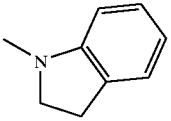 |
| 1.139 | Cl | SO$_2$Me | OCH(Me) | 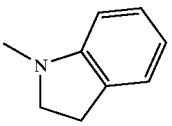 |
| 1.140 | Me | SO$_2$Me | OCH(Me) | 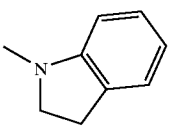 |
| 1.141 | Cl | SO$_2$Et | OCH(Me) | 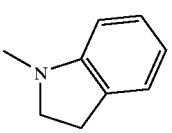 |
| 1.142 | Cl | Cl | OCH(Me) | 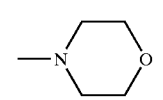 |
| 1.143 | Me | Br | OCH(Me) | 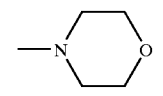 |
| 1.144 | Me | NO$_2$ | OCH(Me) | 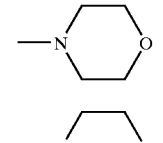 |
| 1.145 | NO$_2$ | Cl | OCH(Me) | 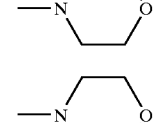 |
| 1.146 | NO$_2$ | Br | OCH(Me) | 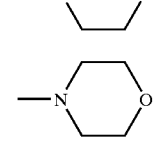 |
| 1.147 | Me | SO$_2$Me | OCH(Me) | 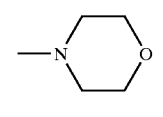 |
| 1.148 | Cl | SO$_2$Et | OCH(Me) | 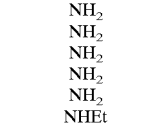 |
| 1.149 | Cl | Cl | OCH$_2$CH$_2$ | NH$_2$ |
| 1.150 | Br | Br | OCH$_2$CH$_2$ | NH$_2$ |
| 1.151 | Me | Br | OCH$_2$CH$_2$ | NH$_2$ |
| 1.152 | Cl | SO$_2$Me | OCH$_2$CH$_2$ | NH$_2$ |
| 1.153 | Cl | SO$_2$Et | OCH$_2$CH$_2$ | NH$_2$ |
| 1.154 | Me | SO$_2$Me | OCH$_2$CH$_2$ | NH$_2$ |
| 1.155 | Cl | Cl | OCH$_2$CH$_2$ | NHEt |
| 1.156 | Cl | SO$_2$Me | OCH$_2$CH$_2$ | NHEt |
| 1.157 | Me | SO$_2$Me | OCH$_2$CH$_2$ | NHEt |
| 1.158 | Br | Br | OCH$_2$CH$_2$ | NH(i-Pr) |
| 1.159 | Me | Br | OCH$_2$CH$_2$ | NH(i-Pr) |
| 1.160 | Me | NO$_2$ | OCH$_2$CH$_2$ | NH(i-Pr) |
| 1.161 | Cl | SO$_2$Et | OCH$_2$CH$_2$ | NH(i-Pr) |
| 1.162 | Cl | Cl | OCH$_2$CH$_2$ | NH(c-Pr) |
| 1.163 | Cl | Br | OCH$_2$CH$_2$ | NH(c-Pr) |
| 1.164 | Me | Br | OCH$_2$CH$_2$ | NH(c-Pr) |
| 1.165 | Me | NO$_2$ | OCH$_2$CH$_2$ | NH(c-Pr) |
| 1.166 | Cl | SO$_2$Me | OCH$_2$CH$_2$ | NH(c-Pr) |
| 1.167 | Cl | Cl | OCH$_2$CH$_2$ | NMe$_2$ |
| 1.168 | Br | Br | OCH$_2$CH$_2$ | NMe$_2$ |
| 1.169 | Cl | Br | OCH$_2$CH$_2$ | NMe$_2$ |
| 1.170 | Me | Br | OCH$_2$CH$_2$ | NMe$_2$ |
| 1.171 | Cl | SO$_2$Me | OCH$_2$CH$_2$ | NMe$_2$ |
| 1.172 | Me | SO$_2$Me | OCH$_2$CH$_2$ | NMe$_2$ |
| 1.173 | Cl | SO$_2$Et | OCH$_2$CH$_2$ | NMe$_2$ |
| 1.174 | Cl | Cl | OCH$_2$CH$_2$ | NEt$_2$ |
| 1.175 | Br | Br | OCH$_2$CH$_2$ | NEt$_2$ |
| 1.176 | Cl | Br | OCH$_2$CH$_2$ | NEt$_2$ |
| 1.177 | Me | Br | OCH$_2$CH$_2$ | NEt$_2$ |
| 1.178 | Cl | SO$_2$Me | OCH$_2$CH$_2$ | NEt$_2$ |
| 1.179 | Me | SO$_2$Me | OCH$_2$CH$_2$ | NEt$_2$ |
| 1.180 | Cl | SO$_2$Et | OCH$_2$CH$_2$ | NEt$_2$ |
| 1.181 | Cl | Cl | OCH$_2$CH$_2$ | N(n-Pr)$_2$ |
| 1.182 | Br | Br | OCH$_2$CH$_2$ | N(n-Pr)$_2$ |
| 1.183 | Cl | Br | OCH$_2$CH$_2$ | N(n-Pr)$_2$ |
| 1.184 | Me | Br | OCH$_2$CH$_2$ | N(n-Pr)$_2$ |
| 1.185 | Cl | SO$_2$Me | OCH$_2$CH$_2$ | N(n-Pr)$_2$ |
| 1.186 | Me | SO$_2$Me | OCH$_2$CH$_2$ | N(n-Pr)$_2$ |
| 1.187 | Cl | SO$_2$Et | OCH$_2$CH$_2$ | N(n-Pr)$_2$ |
| 1.188 | Cl | Cl | OCH$_2$CH$_2$ | N(i-Pr)$_2$ |
| 1.189 | Me | Br | OCH$_2$CH$_2$ | N(i-Pr)$_2$ |
| 1.190 | Me | NO$_2$ | OCH$_2$CH$_2$ | N(i-Pr)$_2$ |
| 1.191 | NO$_2$ | Cl | OCH$_2$CH$_2$ | N(i-Pr)$_2$ |
| 1.192 | NO$_2$ | Br | OCH$_2$CH$_2$ | N(i-Pr)$_2$ |
| 1.193 | Me | SO$_2$Me | OCH$_2$CH$_2$ | N(i-Pr)$_2$ |
| 1.194 | Cl | SO$_2$Et | OCH$_2$CH$_2$ | N(i-Pr)$_2$ |
| 1.195 | Cl | Cl | OCH$_2$CH$_2$ | NmePh |
| 1.196 | Me | Br | OCH$_2$CH$_2$ | NmePh |
| 1.197 | Me | NO$_2$ | OCH$_2$CH$_2$ | NmePh |
| 1.198 | NO$_2$ | Cl | OCH$_2$CH$_2$ | NmePh |
| 1.199 | NO$_2$ | Br | OCH$_2$CH$_2$ | NmePh |
| 1.200 | Me | SO$_2$Me | OCH$_2$CH$_2$ | NmePh |
| 1.201 | Cl | SO$_2$Et | OCH$_2$CH$_2$ | NmePh |
| 1.202 | Cl | Cl | OCH$_2$CH$_2$ | 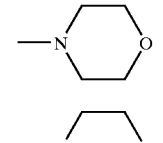 |
| 1.203 | Br | Br | OCH$_2$CH$_2$ | 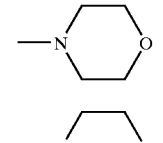 |
| 1.204 | Cl | Br | OCH$_2$CH$_2$ | 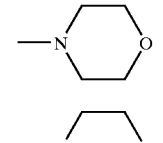 |
| 1.205 | Me | Br | OCH$_2$CH$_2$ | 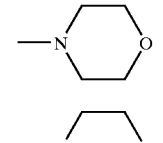 |
| 1.206 | Cl | SO$_2$Me | OCH$_2$CH$_2$ | 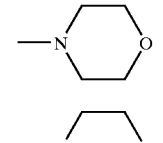 |
| 1.207 | Me | SO$_2$Me | OCH$_2$CH$_2$ | 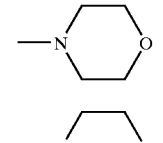 |
| 1.208 | Cl | SO$_2$Et | OCH$_2$CH$_2$ | 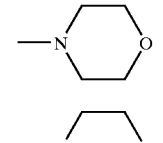 |
| 1.209 | Cl | Cl | OCH$_2$CH$_2$ | 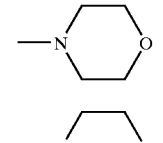 |
| 1.210 | Cl | Cl | OCH$_2$CH=CH | NMe$_2$ |
| 1.211 | Cl | SO$_2$Me | OCH$_2$CH=CH | NMe$_2$ |
| 1.212 | Me | Cl | OCH$_2$CH=CH | NMe$_2$ |

TABLE 1-continued

| | | | | |
|---|---|---|---|---|
| 1.213 | Me | Br | OCH$_2$CH=CH | NMe$_2$ |
| 1.214 | Me | SO$_2$Me | OCH$_2$CH=CH | NMe$_2$ |
| 1.215 | Cl | Cl | OCH$_2$CH=CH | NEt$_2$ |
| 1.216 | Cl | SO$_2$Me | OCH$_2$CH=CH | NEt$_2$ |
| 1.217 | Me | Cl | OCH$_2$CH=CH | NEt$_2$ |
| 1.218 | Me | Br | OCH$_2$CH=CH | NEt$_2$ |
| 1.219 | Me | SO$_2$Me | OCH$_2$CH=CH | NEt$_2$ |
| 1.220 | Cl | Cl | OCH$_2$CH=CH | Nh(c-Pr) |
| 1.221 | Cl | SO$_2$Me | OCH$_2$CH=CH | Nh(c-Pr) |
| 1.222 | Me | Cl | OCH$_2$CH=CH | Nh(c-Pr) |
| 1.223 | Me | Br | OCH$_2$CH=CH | Nh(c-Pr) |
| 1.224 | Me | SO$_2$Me | OCH$_2$CH=CH | Nh(c-Pr) |

TABLE 2

Compounds of the formula (I) according to the invention in which the substituents and symbols are defined as follows:
$R^{1c}$ = H     $R^4$ = H     $R^5$ = Et
$R^6$ = H        Y = O

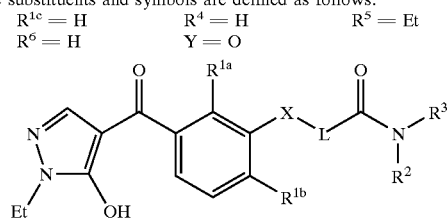

| N | $R^{1a}$ | $R^{1b}$ | X—L | NR$^2$R$^3$ | Physical data |
|---|---|---|---|---|---|
| 2.1 | Cl | Cl | OCH$_2$ | NH$_2$ | |
| 2.2 | Br | Br | OCH$_2$ | NH$_2$ | |
| 2.3 | Me | Br | OCH$_2$ | NH$_2$ | |
| 2.4 | Cl | SO$_2$Me | OCH$_2$ | NH$_2$ | |
| 2.5 | Cl | SO$_2$Et | OCH$_2$ | NH$_2$ | |
| 2.6 | Me | SO$_2$Me | OCH$_2$ | NH$_2$ | |
| 2.6a | Me | Cl | OCH$_2$ | NHMe | |
| 2.6b | Me | Br | OCH$_2$ | NHMe | |
| 2.7 | Cl | Cl | OCH$_2$ | NHEt | |
| 2.8 | Cl | SO$_2$Me | OCH$_2$ | NHEt | |
| 2.8a | Me | Cl | OCH$_2$ | NHEt | |
| 2.8b | Me | Br | OCH$_2$ | NHEt | |
| 2.9 | Me | SO$_2$Me | OCH$_2$ | NHEt | |
| 2.9a | Me | Cl | OCH$_2$ | NH(Allyl) | |
| 2.9b | Me | Br | OCH$_2$ | NH(Allyl) | |
| 2.10 | Br | Br | OCH$_2$ | NH(i-Pr) | |
| 2.11 | Me | Br | OCH$_2$ | NH(i-Pr) | |
| 2.12 | Me | NO$_2$ | OCH$_2$ | NH(i-Pr) | |
| 2.13 | Cl | SO$_2$Et | OCH$_2$ | NH(i-Pr) | |
| 2.14 | Cl | Cl | OCH$_2$ | NH(c-Pr) | |
| 2.15 | Cl | Br | OCH$_2$ | NH(c-Pr) | |
| 2.15a | Me | Cl | OCH$_2$ | NH(c-Pr) | |
| 2.16 | Me | Br | OCH$_2$ | NH(c-Pr) | |
| 2.17 | Me | NO$_2$ | OCH$_2$ | NH(c-Pr) | |
| 2.18 | Cl | SO$_2$Me | OCH$_2$ | NH(c-Pr) | |
| 2.19 | Cl | Cl | OCH$_2$ | NMe$_2$ | R$^f$(EE): 0.27 |
| 2.20 | Br | Br | OCH$_2$ | NMe$_2$ | |
| 2.20a | Me | Cl | OCH$_2$ | NMe$_2$ | R$^f$(EE): 0.01 |
| 2.21 | Cl | Br | OCH$_2$ | NMe$_2$ | |
| 2.22 | Me | Br | OCH$_2$ | NMe$_2$ | |
| 2.23 | Cl | SO$_2$Me | OCH$_2$ | NMe$_2$ | |
| 2.24 | Me | SO$_2$Me | OCH$_2$ | NMe$_2$ | |
| 2.25 | Cl | SO$_2$Et | OCH$_2$ | NMe$_2$ | |
| 2.26 | Cl | Cl | OCH$_2$ | NEt$_2$ | |
| 2.27 | Br | Br | OCH$_2$ | NEt$_2$ | |
| 2.27a | Me | Cl | OCH$_2$ | NEt$_2$ | R$^f$(EE): 0.01 |
| 2.28 | Cl | Br | OCH$_2$ | NEt$_2$ | |
| 2.29 | Me | Br | OCH$_2$ | NEt$_2$ | |
| 2.30 | Cl | SO$_2$Me | OCH$_2$ | NEt$_2$ | R$^f$(EE): 0.04 |
| 2.31 | Me | SO$_2$Me | OCH$_2$ | NEt$_2$ | |
| 2.32 | Cl | SO$_2$Et | OCH$_2$ | NEt$_2$ | |
| 2.33 | Cl | Cl | OCH$_2$ | N(n-Pr)$_2$ | |
| 2.34 | Br | Br | OCH$_2$ | N(n-Pr)$_2$ | |
| 2.35 | Cl | Br | OCH$_2$ | N(n-Pr)$_2$ | |
| 2.36 | Me | Br | OCH$_2$ | N(n-Pr)$_2$ | |
| 2.37 | Cl | SO$_2$Me | OCH$_2$ | N(n-Pr)$_2$ | |
| 2.38 | Me | SO$_2$Me | OCH$_2$ | N(n-Pr)$_2$ | |
| 2.39 | Cl | SO$_2$Et | OCH$_2$ | N(n-Pr)$_2$ | |
| 2.41 | Me | Br | OCH$_2$ | N(i-Pr)$_2$ | |
| 2.42 | Me | NO$_2$ | OCH$_2$ | N(i-Pr)$_2$ | |
| 2.43 | NO$_2$ | Cl | OCH$_2$ | N(i-Pr)$_2$ | |
| 2.44 | NO$_2$ | Br | OCH$_2$ | N(i-Pr)$_2$ | |
| 2.45 | Me | SO$_2$Me | OCH$_2$ | N(i-Pr)$_2$ | |
| 2.46 | Cl | SO$_2$Et | OCH$_2$ | N(i-Pr)$_2$ | |
| 2.47 | Cl | Cl | OCH$_2$ | NmePh | |
| 2.48 | Me | Br | OCH$_2$ | NmePh | |
| 2.49 | Me | NO$_2$ | OCH$_2$ | NmePh | |
| 2.50 | NO$_2$ | Cl | OCH$_2$ | NmePh | |
| 2.51 | NO$_2$ | Br | OCH$_2$ | NmePh | |
| 2.52 | Me | SO$_2$Me | OCH$_2$ | NmePh | |
| 2.53 | Cl | SO$_2$Et | OCH$_2$ | NmePh | |
| 2.54 | Cl | Cl | OCH$_2$ | 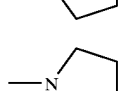 | |
| 2.55 | Br | Br | OCH$_2$ | 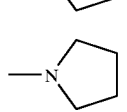 | |
| 2.56 | Cl | Br | OCH$_2$ | 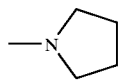 | |
| 2.57 | Me | Br | OCH$_2$ | 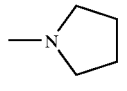 | |
| 2.58 | Cl | SO$_2$Me | OCH$_2$ | 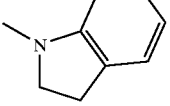 | |
| 2.59 | Me | SO$_2$Me | OCH$_2$ | 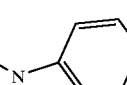 | |
| 2.60 | Cl | SO$_2$Et | OCH$_2$ | 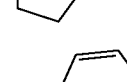 | |
| 2.61 | Cl | Cl | OCH$_2$ | 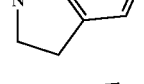 | |
| 2.62 | Br | Br | OCH$_2$ | 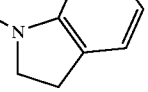 | |
| 2.63 | Cl | Br | OCH$_2$ | | |
| 2.64 | Me | Br | OCH$_2$ | | |

TABLE 2-continued

| | | | | |
|---|---|---|---|---|
| 2.65 | Cl | SO₂Me | OCH₂ | 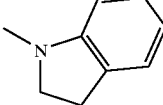 |
| 2.66 | Me | SO₂Me | OCH₂ | 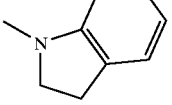 |
| 2.67 | Cl | SO₂Et | OCH₂ | 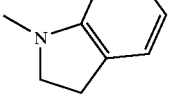 |
| 2.68 | Cl | Cl | OCH₂ | 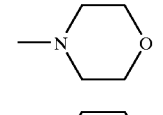 |
| 2.69 | Me | Br | OCH₂ | 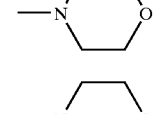 |
| 2.70 | Me | NO₂ | OCH₂ | 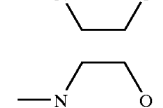 |
| 2.71 | NO₂ | Cl | OCH₂ | 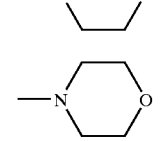 |
| 2.72 | NO₂ | Br | OCH₂ | 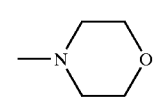 |
| 2.73 | Me | SO₂Me | OCH₂ | 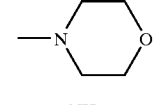 |
| 2.74 | Cl | SO₂Et | OCH₂ | 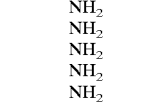 |
| 2.75 | Cl | Cl | OCH(Me) | NH₂ |
| 2.76 | Br | Br | OCH(Me) | NH₂ |
| 2.77 | Me | Br | OCH(Me) | NH₂ |
| 2.78 | Cl | SO₂Me | OCH(Me) | NH₂ |
| 2.79 | Cl | SO₂Et | OCH(Me) | NH₂ |
| 2.80 | Me | SO₂Me | OCH(Me) | NH₂ |
| 2.80a | Cl | Cl | OCH(Me) | NHMe | R$^f$(EE): 0.26 |
| 2.80b | Cl | SO₂Me | OCH(Me) | NHMe |
| 2.80c | Me | Cl | OCH(Me) | NHMe |
| 2.80d | Me | Br | OCH(Me) | NHMe |
| 2.80e | Me | SO₂Me | OCH(Me) | NHMe |
| 2.81 | Cl | Cl | OCH(Me) | NHEt | R$^f$(EE): 0.01 |
| 2.82 | Cl | SO₂Me | OCH(Me) | NHEt |
| 2.82a | Me | Cl | OCH(Me) | NHEt |
| 2.82b | Me | Br | OCH(Me) | NHEt |
| 2.82c | Cl | Cl | OCH(Me) | NH(Allyl) |
| 2.82d | Cl | SO₂Me | OCH(Me) | NH(Allyl) |
| 2.82e | Me | Cl | OCH(Me) | NH(Allyl) |
| 2.82f | Me | Br | OCH(Me) | NH(Allyl) |
| 2.82g | Me | SO₂Me | OCH(Me) | NH(Allyl) |
| 2.83 | Me | SO₂Me | OCH(Me) | NHEt |
| 2.84 | Br | Br | OCH(Me) | NH(i-Pr) |
| 2.85 | Me | Br | OCH(Me) | NH(i-Pr) |
| 2.86 | Me | NO₂ | OCH(Me) | NH(i-Pr) |
| 2.87 | Cl | SO₂Et | OCH(Me) | NH(i-Pr) |
| 2.88 | Cl | Cl | OCH(Me) | NH(c-Pr) | R$^f$(EE): 0.03 |
| 2.89 | Cl | Br | OCH(Me) | NH(c-Pr) |
| 2.90 | Me | Br | OCH(Me) | NH(c-Pr) |
| 2.91 | Me | NO₂ | OCH(Me) | NH(c-Pr) |
| 2.92 | Cl | SO₂Me | OCH(Me) | NH(c-Pr) |
| 2.93 | Cl | Cl | OCH(Me) | NMe₂ | R$^f$(EE): 0.28 |
| 2.94 | Br | Br | OCH(Me) | NMe₂ |
| 2.95 | Cl | Br | OCH(Me) | NMe₂ |
| 2.96 | Me | Br | OCH(Me) | NMe₂ | R$^f$(EE): 0.04 |
| 2.97 | Cl | SO₂Me | OCH(Me) | NMe₂ |
| 2.98 | Me | SO₂Me | OCH(Me) | NMe₂ |
| 2.99 | Cl | SO₂Et | OCH(Me) | NMe₂ |
| 2.100 | Cl | Cl | OCH(Me) | NEt₂ |
| 2.101 | Br | Br | OCH(Me) | NEt₂ |
| 2.102 | Cl | Br | OCH(Me) | NEt₂ |
| 2.103 | Me | Br | OCH(Me) | NEt₂ |
| 2.104 | Cl | SO₂Me | OCH(Me) | NEt₂ |
| 2.105 | Me | SO₂Me | OCH(Me) | NEt₂ |
| 2.106 | Cl | SO₂Et | OCH(Me) | NEt₂ |
| 2.107 | Cl | Cl | OCH(Me) | N(n-Pr)₂ |
| 2.108 | Br | Br | OCH(Me) | N(n-Pr)₂ |
| 2.109 | Cl | Br | OCH(Me) | N(n-Pr)₂ |
| 2.110 | Me | Br | OCH(Me) | N(n-Pr)₂ |
| 2.111 | Cl | SO₂Me | OCH(Me) | N(n-Pr)₂ |
| 2.112 | Me | SO₂Me | OCH(Me) | N(n-Pr)₂ |
| 2.113 | Cl | SO₂Et | OCH(Me) | N(n-Pr)₂ |
| 2.114 | Cl | Cl | OCH(Me) | N(i-Pr)₂ |
| 2.115 | Me | Br | OCH(Me) | N(i-Pr)₂ |
| 2.116 | Me | NO₂ | OCH(Me) | N(i-Pr)₂ |
| 2.117 | NO₂ | Cl | OCH(Me) | N(i-Pr)₂ |
| 2.118 | NO₂ | Br | OCH(Me) | N(i-Pr)₂ |
| 2.119 | Me | SO₂Me | OCH(Me) | NmePh |
| 2.120 | Cl | SO₂Et | OCH(Me) | NmePh |
| 2.121 | Cl | Cl | OCH(Me) | NmePh |
| 2.122 | Me | Br | OCH(Me) | NmePh |
| 2.123 | Me | NO₂ | OCH(Me) | NmePh |
| 2.124 | NO₂ | Cl | OCH(Me) | NmePh |
| 2.125 | NO₂ | Br | OCH(Me) | NmePh |
| 2.126 | Me | SO₂Me | OCH(Me) | NmePh |
| 2.127 | Cl | SO₂Et | OCH(Me) | NmePh |
| 2.128 | Cl | Cl | OCH(Me) | 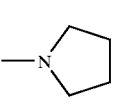 |
| 2.129 | Br | Br | OCH(Me) | 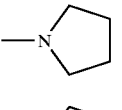 |
| 2.130 | Cl | Br | OCH(Me) | 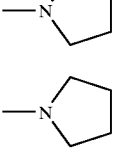 |
| 2.131 | Me | Br | OCH(Me) |  |
| 2.132 | Cl | SO₂Me | OCH(Me) |  |
| 2.133 | Me | SO₂Me | OCH(Me) | 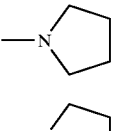 |
| 2.134 | Cl | SO₂Et | OCH(Me) | 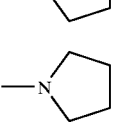 |

TABLE 2-continued

| | | | | |
|---|---|---|---|---|
| 2.135 | Cl | Cl | OCH(Me) | 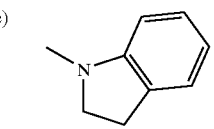 |
| 2.136 | Br | Br | OCH(Me) | 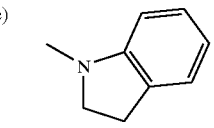 |
| 2.137 | Cl | Br | OCH(Me) | 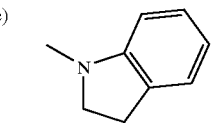 |
| 2.138 | Me | Br | OCH(Me) | 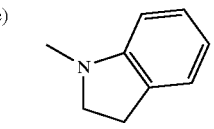 |
| 2.139 | Cl | SO$_2$Me | OCH(Me) | 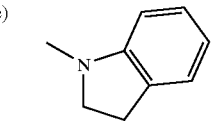 |
| 2.140 | Me | SO$_2$Me | OCH(Me) | 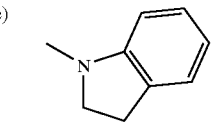 |
| 2.141 | Cl | SO$_2$Et | OCH(Me) | 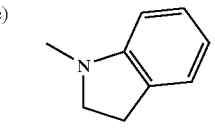 |
| 2.142 | Cl | Cl | OCH(Me) | 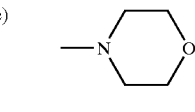 |
| 2.143 | Me | Br | OCH(Me) | 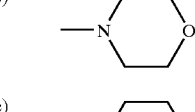 |
| 2.144 | Me | NO$_2$ | OCH(Me) | 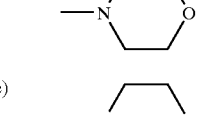 |
| 2.145 | NO$_2$ | Cl | OCH(Me) | 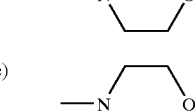 |
| 2.146 | NO$_2$ | Br | OCH(Me) | 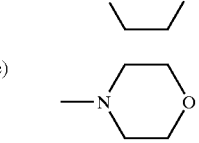 |
| 2.147 | Me | SO$_2$Me | OCH(Me) |  |

TABLE 2-continued

| | | | | |
|---|---|---|---|---|
| 2.148 | Cl | SO$_2$Et | OCH(Me) |  |
| 2.149 | Cl | Cl | OCH$_2$CH$_2$ | NH$_2$ |
| 2.150 | Br | Br | OCH$_2$CH$_2$ | NH$_2$ |
| 2.151 | Me | Br | OCH$_2$CH$_2$ | NH$_2$ |
| 2.152 | Cl | SO$_2$Me | OCH$_2$CH$_2$ | NH$_2$ |
| 2.153 | Cl | SO$_2$Et | OCH$_2$CH$_2$ | NH$_2$ |
| 2.154 | Me | SO$_2$Me | OCH$_2$CH$_2$ | NH$_2$ |
| 2.155 | Cl | Cl | OCH$_2$CH$_2$ | NHEt |
| 2.156 | Cl | SO$_2$Me | OCH$_2$CH$_2$ | NHEt |
| 2.157 | Me | SO$_2$Me | OCH$_2$CH$_2$ | NHEt |
| 2.158 | Br | Br | OCH$_2$CH$_2$ | NH(i-Pr) |
| 2.159 | Me | Br | OCH$_2$CH$_2$ | NH(i-Pr) |
| 2.160 | Me | NO$_2$ | OCH$_2$CH$_2$ | NH(i-Pr) |
| 2.161 | Cl | SO$_2$Et | OCH$_2$CH$_2$ | NH(i-Pr) |
| 2.162 | Cl | Cl | OCH$_2$CH$_2$ | NH(c-Pr) |
| 2.163 | Cl | Br | OCH$_2$CH$_2$ | NH(c-Pr) |
| 2.164 | Me | Br | OCH$_2$CH$_2$ | NH(c-Pr) |
| 2.165 | Me | NO$_2$ | OCH$_2$CH$_2$ | NH(c-Pr) |
| 2.166 | Cl | SO$_2$Me | OCH$_2$CH$_2$ | NH(c-Pr) |
| 2.167 | Cl | Cl | OCH$_2$CH$_2$ | NMe$_2$ |
| 2.168 | Br | Br | OCH$_2$CH$_2$ | NMe$_2$ |
| 2.169 | Cl | Br | OCH$_2$CH$_2$ | NMe$_2$ |
| 2.170 | Me | Br | OCH$_2$CH$_2$ | NMe$_2$ |
| 2.171 | Cl | SO$_2$Me | OCH$_2$CH$_2$ | NMe$_2$ |
| 2.172 | Me | SO$_2$Me | OCH$_2$CH$_2$ | NMe$_2$ |
| 2.173 | Cl | SO$_2$Et | OCH$_2$CH$_2$ | NMe$_2$ |
| 2.174 | Cl | Cl | OCH$_2$CH$_2$ | NEt$_2$ |
| 2.175 | Br | Br | OCH$_2$CH$_2$ | NEt$_2$ |
| 2.176 | Cl | Br | OCH$_2$CH$_2$ | NEt$_2$ |
| 2.177 | Me | Br | OCH$_2$CH$_2$ | NEt$_2$ |
| 2.178 | Cl | SO$_2$Me | OCH$_2$CH$_2$ | NEt$_2$ |
| 2.179 | Me | SO$_2$Me | OCH$_2$CH$_2$ | NEt$_2$ |
| 2.180 | Cl | SO$_2$Et | OCH$_2$CH$_2$ | NEt$_2$ |
| 2.181 | Cl | Cl | OCH$_2$CH$_2$ | N(n-Pr)$_2$ |
| 2.182 | Br | Br | OCH$_2$CH$_2$ | N(n-Pr)$_2$ |
| 2.183 | Cl | Br | OCH$_2$CH$_2$ | N(n-Pr)$_2$ |
| 2.184 | Me | Br | OCH$_2$CH$_2$ | N(n-Pr)$_2$ |
| 2.185 | Cl | SO$_2$Me | OCH$_2$CH$_2$ | N(n-Pr)$_2$ |
| 2.186 | Me | SO$_2$Me | OCH$_2$CH$_2$ | N(n-Pr)$_2$ |
| 2.187 | Cl | SO$_2$Et | OCH$_2$CH$_2$ | N(n-Pr)$_2$ |
| 2.188 | Cl | Cl | OCH$_2$CH$_2$ | N(i-Pr)$_2$ |
| 2.189 | Me | Br | OCH$_2$CH$_2$- | N(i-Pr)$_2$ |
| 2.190 | Me | NO$_2$ | OCH$_2$CH$_2$ | N(i-Pr)$_2$ |
| 2.191 | NO$_2$ | Cl | OCH$_2$CH$_2$ | N(i-Pr)$_2$ |
| 2.192 | NO$_2$ | Br | OCH$_2$CH$_2$ | N(i-Pr)$_2$ |
| 2.193 | Me | SO$_2$Me | OCH$_2$CH$_2$ | N(i-Pr)$_2$ |
| 2.194 | Cl | SO$_2$Et | OCH$_2$CH$_2$ | N(i-Pr)$_2$ |
| 2.195 | Cl | Cl | OCH$_2$CH$_2$ | NmePh |
| 2.196 | Me | Br | OCH$_2$CH$_2$ | NmePh |
| 2.197 | Me | NO$_2$ | OCH$_2$CH$_2$ | NmePh |
| 2.198 | NO$_2$ | Cl | OCH$_2$CH$_2$ | NmePh |
| 2.199 | NO$_2$ | Br | OCH$_2$CH$_2$ | NmePh |
| 2.200 | Me | SO$_2$Me | OCH$_2$CH$_2$ | NmePh |
| 2.201 | Cl | SO$_2$Et | OCH$_2$CH$_2$ | NmePh |
| 2.202 | Cl | Cl | OCH$_2$CH$_2$ |  |
| 2.203 | Br | Br | OCH$_2$CH$_2$ |  |
| 2.204 | Cl | Br | OCH$_2$CH$_2$ |  |
| 2.205 | Me | Br | OCH$_2$CH$_2$ |  |

TABLE 2-continued

| 2.206 | Cl | SO₂Me | OCH₂CH₂ | 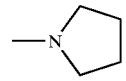 |
| 2.207 | Me | SO₂Me | OCH₂CH₂ | 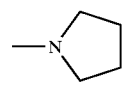 |
| 2.208 | Cl | SO₂Et | OCH₂CH₂ | 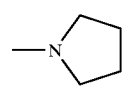 |
| 2.209 | Cl | Cl | OCH₂CH=CH | NMe₂ |
| 2.210 | Cl | SO₂Me | OCH₂CH=CH | NMe₂ |
| 2.211 | Me | Cl | OCH₂CH=CH | NMe₂ |
| 2.212 | Me | Br | OCH₂CH=CH | NMe₂ |
| 2.213 | Me | SO₂Me | OCH₂CH=CH | NMe₂ |
| 2.214 | Cl | Cl | OCH₂CH=CH | NEt₂ |
| 2.215 | Cl | SO₂Me | OCH₂CH=CH | NEt₂ |
| 2.216 | Me | Cl | OCH₂CH=CH | NEt₂ |
| 2.217 | Me | Br | OCH₂CH=CH | NEt₂ |
| 2.218 | Me | SO₂Me | OCH₂CH=CH | NEt₂ |
| 2.219 | Cl | Cl | OCH₂CH=CH | Nh(c-Pr) |
| 2.220 | Cl | SO₂Me | OCH₂CH=CH | Nh(c-Pr) |
| 2.221 | Me | Cl | OCH₂CH=CH | Nh(c-Pr) |
| 2.222 | Me | Br | OCH₂CH=CH | Nh(c-Pr) |
| 2.223 | Me | SO₂Me | OCH₂CH=CH | Nh(c-Pr) |

TABLE 3

Compounds of the formula (I) according to the invention in which the substituents and symbols have the following definitions:
$R^{1c} = H$   $R^4 = Me$   $R^5 = Me$
$R^6 = H$   $Y = O$

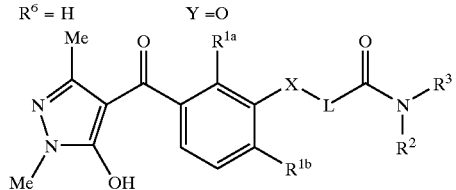

| No. | $R^{1a}$ | $R^{1b}$ | X—L | $NR^2R^3$ | Physical data |
|---|---|---|---|---|---|
| 3.1 | Cl | Cl | OCH₂ | NH₂ | |
| 3.2 | Br | Br | OCH₂ | NH₂ | |
| 3.3 | Me | Br | OCH₂ | NH₂ | |
| 3.4 | Cl | SO₂Me | OCH₂ | NH₂ | |
| 3.5 | Cl | SO₂Et | OCH₂ | NH₂ | |
| 3.6 | Me | SO₂Me | OCH₂ | NH₂ | |
| 3.6a | Me | Cl | OCH₂ | NHMe | |
| 3.6b | Me | Br | OCH₂ | NHMe | $R^f(EE)$: 0.28 |
| 3.7 | Cl | Cl | OCH₂ | NHEt | |
| 3.8 | Cl | SO₂Me | OCH₂ | NHEt | |
| 3.8a | Me | Cl | OCH₂ | NHEt | |
| 3.8b | Me | Br | OCH₂ | NHEt | $R^f(EE)$: 0.28 |
| 3.9 | Me | SO₂Me | OCH₂ | NHEt | |
| 3.9a | Me | Cl | OCH₂ | NH(Allyl) | |
| 3.9b | Me | Br | OCH₂ | NH(Allyl) | |
| 3.10 | Br | Br | OCH₂ | NH(i-Pr) | |
| 3.11 | Me | Br | OCH₂ | NH(i-Pr) | |
| 3.12 | Me | NO2 | OCH₂ | NH(i-Pr) | |
| 3.13 | Cl | SO₂Et | OCH₂ | NH(i-Pr) | |
| 3.14 | Cl | Cl | OCH₂ | NH(c-Pr) | |
| 3.15 | Cl | Br | OCH₂ | NH(c-Pr) | |
| 3.15a | Me | Cl | OCH₂ | NH(c-Pr) | |
| 3.16 | Me | Br | OCH₂ | NH(c-Pr) | |
| 3.17 | Me | NO2 | OCH₂ | NH(c-Pr) | |
| 3.18 | Cl | SO₂Me | OCH₂ | NH(c-Pr) | |
| 3.19 | Cl | Cl | OCH₂ | NMe₂ | |

TABLE 3-continued

| 3.20 | Br | Br | OCH₂ | NMe₂ | |
| 3.20a | Me | Cl | OCH₂ | NMe₂ | $R^f(EE)$: 0.02 |
| 3.21 | Cl | Br | OCH₂ | NMe₂ | |
| 3.22 | Me | Br | OCH₂ | NMe₂ | |
| 3.23 | Cl | SO₂Me | OCH₂ | NMe₂ | |
| 3.24 | Me | SO₂Me | OCH₂ | NMe₂ | |
| 3.25 | Cl | SO₂Et | OCH₂ | NMe₂ | |
| 3.26 | Cl | Cl | OCH₂ | NEt₂ | |
| 3.27 | Br | Br | OCH₂ | NEt₂ | |
| 3.27a | Me | Cl | OCH₂ | NEt₂ | $R^f(EE)$: 0.03 |
| 3.28 | Cl | Br | OCH₂ | NEt₂ | |
| 3.29 | Me | Br | OCH₂ | NEt₂ | |
| 3.30 | Cl | SO₂Me | OCH₂ | NEt₂ | |
| 3.31 | Me | SO₂Me | OCH₂ | NEt₂ | |
| 3.32 | Cl | SO₂Et | OCH₂ | NEt₂ | |
| 3.33 | Cl | Cl | OCH₂ | N(n-Pr)₂ | |
| 3.34 | Br | Br | OCH₂ | N(n-Pr)₂ | |
| 3.35 | Cl | Br | OCH₂ | N(n-Pr)₂ | |
| 3.36 | Me | Br | OCH₂ | N(n-Pr)₂ | |
| 3.37 | Cl | SO₂Me | OCH₂ | N(n-Pr)₂ | $R^f(EE)$: 0.02 |
| 3.38 | Me | SO₂Me | OCH₂ | N(n-Pr)₂ | |
| 3.39 | Cl | SO₂Et | OCH₂ | N(n-Pr)₂ | |
| 3.40 | Cl | Cl | OCH₂ | N(i-Pr)₂ | |
| 3.41 | Me | Br | OCH₂ | N(i-Pr)₂ | |
| 3.42 | Me | NO₂ | OCH₂ | N(i-Pr)₂ | |
| 3.43 | NO₂ | Cl | OCH₂ | N(i-Pr)₂ | |
| 3.44 | NO₂ | Br | OCH₂ | N(i-Pr)₂ | |
| 3.45 | Me | SO₂Me | OCH₂ | N(i-Pr)₂ | |
| 3.46 | Cl | SO₂Et | OCH₂ | N(i-Pr)₂ | |
| 3.47 | Cl | Cl | OCH₂ | NmePh | |
| 3.48 | Me | Br | OCH₂ | NmePh | |
| 3.49 | Me | NO₂ | OCH₂ | NmePh | |
| 3.50 | NO₂ | Cl | OCH₂ | NmePh | |
| 3.51 | NO₂ | Br | OCH₂ | NmePh | |
| 3.52 | Me | SO₂Me | OCH₂ | NmePh | |
| 3.53 | Cl | SO₂Et | OCH₂ | NmePh | |
| 3.54 | Cl | Cl | OCH₂ |  | |
| 3.55 | Br | Br | OCH₂ |  | $R^f(EE)$: 0.01 |
| 3.56 | Cl | Br | OCH₂ |  | |
| 3.57 | Me | Br | OCH₂ |  | |
| 3.58 | Cl | SO₂Me | OCH₂ |  | |
| 3.59 | Me | SO₂Me | OCH₂ |  | |
| 3.60 | Cl | SO₂Et | OCH₂ |  | |
| 3.61 | Cl | Cl | OCH₂ |  | |

TABLE 3-continued

| | | | | |
|---|---|---|---|---|
| 3.62 | Br | Br | OCH$_2$ | 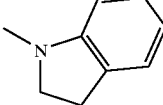 |
| 3.63 | Cl | Br | OCH$_2$ | 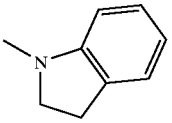 |
| 3.64 | Me | Br | OCH$_2$ | 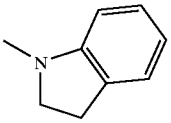 |
| 3.65 | Cl | SO$_2$Me | OCH$_2$ | 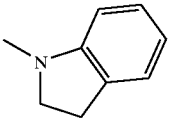 |
| 3.66 | Me | SO$_2$Me | OCH$_2$ | 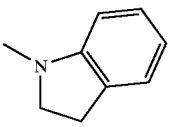 |
| 3.67 | Cl | SO$_2$Et | OCH$_2$ | 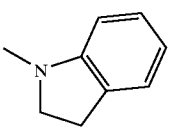 |
| 3.68 | Cl | Cl | OCH$_2$ | 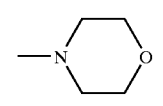 |
| 3.69 | Me | Br | OCH$_2$ | 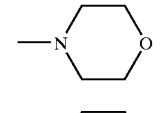 |
| 3.70 | Me | NO$_2$ | OCH$_2$ | 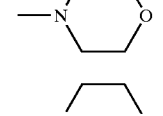 |
| 3.71 | NO$_2$ | Cl | OCH$_2$ | 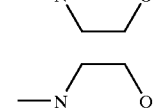 |
| 3.72 | NO$_2$ | Br | OCH$_2$ | 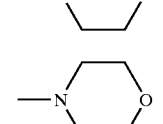 |
| 3.73 | Me | SO$_2$Me | OCH$_2$ | 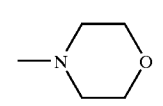 |
| 3.74 | Cl | SO$_2$Et | OCH$_2$ | 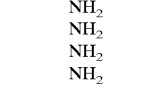 |
| 3.75 | Cl | Cl | OCH(Me) | NH$_2$ |
| 3.76 | Br | Br | OCH(Me) | NH$_2$ |
| 3.77 | Me | Br | OCH(Me) | NH$_2$ |
| 3.78 | Cl | SO$_2$Me | OCH(Me) | NH$_2$ |

TABLE 3-continued

| | | | | | |
|---|---|---|---|---|---|
| 3.79 | Cl | SO$_2$Et | OCH(Me) | NH$_2$ | |
| 3.80 | Me | SO$_2$Me | OCH(Me) | NH$_2$ | |
| 3.80a | Cl | Cl | OCH(Me) | NHMe | |
| 3.80b | Cl | SO$_2$Me | OCH(Me) | NHMe | |
| 3.80c | Me | Cl | OCH(Me) | NHMe | |
| 3.80d | Me | Br | OCH(Me) | NHMe | |
| 3.80e | Me | SO$_2$Me | OCH(Me) | NHMe | |
| 3.81 | Cl | Cl | OCH(Me) | NHEt | R$^f$(EE): 0.35 |
| 3.82 | Cl | SO$_2$Me | OCH(Me) | NHEt | |
| 3.82a | Me | Cl | OCH(Me) | NHEt | |
| 3.82b | Me | Br | OCH(Me) | NHEt | |
| 3.82c | Cl | Cl | OCH(Me) | NH(Allyl) | R$^f$(EE): 0.05 |
| 3.82d | Cl | SO$_2$Me | OCH(Me) | NH(Allyl) | |
| 3.82e | Me | Cl | OCH(Me) | NH(Allyl) | |
| 3.82f | Me | Br | OCH(Me) | NH(Allyl) | |
| 3.82g | Me | SO$_2$Me | OCH(Me) | NH(Allyl) | |
| 3.83 | Me | SO$_2$Me | OCH(Me) | NHEt | |
| 3.84 | Br | Br | OCH(Me) | NH(i-Pr) | |
| 3.85 | Me | Br | OCH(Me) | NH(i-Pr) | R$^f$(EE): 0.11 |
| 3.86 | Me | NO$_2$ | OCH(Me) | NH(i-Pr) | |
| 3.87 | Cl | SO$_2$Et | OCH(Me) | NH(i-Pr) | |
| 3.88 | Cl | Cl | OCH(Me) | NH(c-Pr) | R$^f$(EE): 0.10 |
| 3.89 | Cl | Br | OCH(Me) | NH(c-Pr) | |
| 3.90 | Me | Br | OCH(Me) | NH(c-Pr) | |
| 3.91 | Me | NO$_2$ | OCH(Me) | NH(c-Pr) | |
| 3.92 | Cl | SO$_2$Me | OCH(Me) | NH(c-Pr) | |
| 3.93 | Cl | Cl | OCH(Me) | NMe$_2$ | |
| 3.94 | Br | Br | OCH(Me) | NMe$_2$ | |
| 3.95 | Cl | Br | OCH(Me) | NMe$_2$ | |
| 3.96 | Me | Br | OCH(Me) | NMe$_2$ | R$^f$(EE): 0.18 |
| 3.97 | Cl | SO$_2$Me | OCH(Me) | NMe$_2$ | |
| 3.98 | Me | SO$_2$Me | OCH(Me) | NMe$_2$ | |
| 3.99 | Cl | SO$_2$Et | OCH(Me) | NMe$_2$ | |
| 3.100 | Cl | Cl | OCH(Me) | NEt$_2$ | |
| 3.101 | Br | Br | OCH(Me) | NEt$_2$ | |
| 3.102 | Cl | Br | OCH(Me) | NEt$_2$ | |
| 3.103 | Me | Br | OCH(Me) | NEt$_2$ | |
| 3.104 | Cl | SO$_2$Me | OCH(Me) | NEt$_2$ | |
| 3.105 | Me | SO$_2$Me | OCH(Me) | NEt$_2$ | |
| 3.106 | Cl | SO$_2$Et | OCH(Me) | NEt$_2$ | |
| 3.107 | Cl | Cl | OCH(Me) | N(n-Pr)$_2$ | |
| 3.108 | Br | Br | OCH(Me) | N(n-Pr)$_2$ | |
| 3.109 | Cl | Br | OCH(Me) | N(n-Pr)$_2$ | |
| 3.110 | Me | Br | OCH(Me) | N(n-Pr)$_2$ | |
| 3.111 | Cl | SO$_2$Me | OCH(Me) | N(n-Pr)$_2$ | |
| 3.112 | Me | SO$_2$Me | OCH(Me) | N(n-Pr)$_2$ | |
| 3.113 | Cl | SO$_2$Et | OCH(Me) | N(n-Pr)$_2$ | |
| 3.114 | Cl | Cl | OCH(Me) | N(i-Pr)$_2$ | |
| 3.115 | Me | Br | OCH(Me) | N(i-Pr)$_2$ | |
| 3.116 | Me | NO$_2$ | OCH(Me) | N(i-Pr)$_2$ | |
| 3.117 | NO$_2$ | Cl | OCH(Me) | N(i-Pr)$_2$ | |
| 3.118 | NO$_2$ | Br | OCH(Me) | N(i-Pr)$_2$ | |
| 3.119 | Me | SO$_2$Me | OCH(Me) | N(i-Pr)$_2$ | |
| 3.120 | Cl | SO$_2$Et | OCH(Me) | N(i-Pr)$_2$ | |
| 3.121 | Cl | Cl | OCH(Me) | NmePh | |
| 3.122 | Me | Br | OCH(Me) | NmePh | |
| 3.123 | Me | NO$_2$ | OCH(Me) | NmePh | |
| 3.124 | NO$_2$ | Cl | OCH(Me) | NmePh | |
| 3.125 | NO$_2$ | Br | OCH(Me) | NmePh | |
| 3.126 | Me | SO$_2$Me | OCH(Me) | NmePh | |
| 3.127 | Cl | SO$_2$Et | OCH(Me) | NmePh | |
| 3.128 | Cl | Cl | OCH(Me) | 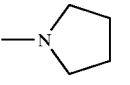 | |
| 3.129 | Br | Br | OCH(Me) | 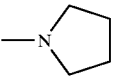 | |
| 3.130 | Cl | Br | OCH(Me) | 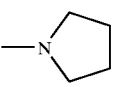 | |

TABLE 3-continued

| | | | | |
|---|---|---|---|---|
| 3.131 | Me | Br | OCH(Me) | 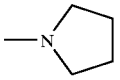 |
| 3.132 | Cl | SO$_2$Me | OCH(Me) | 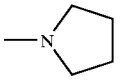 |
| 3.133 | Me | SO$_2$Me | OCH(Me) | 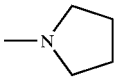 |
| 3.134 | Cl | SO$_2$Et | OCH(Me) | 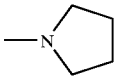 |
| 3.135 | Cl | Cl | OCH(Me) | 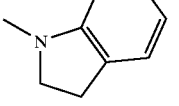 |
| 3.136 | Br | Br | OCH(Me) | 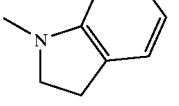 |
| 3.137 | Cl | Br | OCH(Me) | 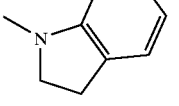 |
| 3.138 | Me | Br | OCH(Me) | 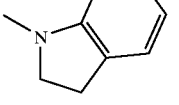 |
| 3.139 | Cl | SO$_2$Me | OCH(Me) | 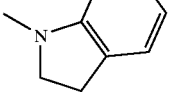 |
| 3.140 | Me | SO$_2$Me | OCH(Me) | 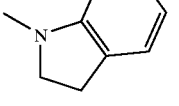 |
| 3.141 | Cl | SO$_2$Et | OCH(Me) | 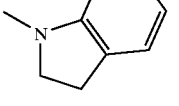 |
| 3.142 | Cl | Cl | OCH(Me) | 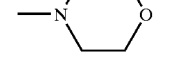 |
| 3.143 | Me | Br | OCH(Me) | 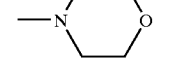 |
| 3.144 | Me | NO$_2$ | OCH(Me) | 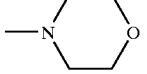 |
| 3.145 | NO$_2$ | Cl | OCH(Me) |  |
| 3.146 | NO$_2$ | Br | OCH(Me) |  |
| 3.147 | Me | SO$_2$Me | OCH(Me) |  |
| 3.148 | Cl | SO$_2$Et | OCH(Me) |  |
| 3.149 | Cl | Cl | OCH$_2$CH$_2$ | NH$_2$ |
| 3.150 | Br | Br | OCH$_2$CH$_2$ | NH$_2$ |
| 3.151 | Me | Br | OCH$_2$CH$_2$ | NH$_2$ |
| 3.152 | Cl | SO$_2$Me | OCH$_2$CH$_2$ | NH$_2$ |
| 3.153 | Cl | SO$_2$Et | OCH$_2$CH$_2$ | NH$_2$ |
| 3.154 | Me | SO$_2$Me | OCH$_2$CH$_2$ | NH$_2$ |
| 3.155 | Cl | Cl | OCH$_2$CH$_2$ | NHEt |
| 3.156 | Cl | SO$_2$Me | OCH$_2$CH$_2$ | NHEt |
| 3.157 | Me | SO$_2$Me | OCH$_2$CH$_2$ | NHEt |
| 3.158 | Br | Br | OCH$_2$CH$_2$ | NH(i-Pr) |
| 3.159 | Me | Br | OCH$_2$CH$_2$ | NH(i-Pr) |
| 3.160 | Me | NO$_2$ | OCH$_2$CH$_2$ | NH(i-Pr) |
| 3.161 | Cl | SO$_2$Et | OCH$_2$CH$_2$ | NH(i-Pr) |
| 3.162 | Cl | Cl | OCH$_2$CH$_2$ | NH(c-Pr) |
| 3.163 | Cl | Br | OCH$_2$CH$_2$ | NH(c-Pr) |
| 3.164 | Me | Br | OCH$_2$CH$_2$ | NH(c-Pr) |
| 3.165 | Me | NO$_2$ | OCH$_2$CH$_2$ | NH(c-Pr) |
| 3.166 | Cl | SO$_2$Me | OCH$_2$CH$_2$ | NH(c-Pr) |
| 3.167 | Cl | Cl | OCH$_2$CH$_2$ | NMe$_2$ |
| 3.168 | Br | Br | OCH$_2$CH$_2$ | NMe$_2$ |
| 3.169 | Cl | Br | OCH$_2$CH$_2$ | NMe$_2$ |
| 3.170 | Me | Br | OCH$_2$CH$_2$ | NMe$_2$ |
| 3.171 | Cl | SO$_2$Me | OCH$_2$CH$_2$ | NMe$_2$ |
| 3.172 | Me | SO$_2$Me | OCH$_2$CH$_2$ | NMe$_2$ |
| 3.173 | Cl | SO$_2$Et | OCH$_2$CH$_2$ | NMe$_2$ |
| 3.174 | Cl | Cl | OCH$_2$CH$_2$ | NEt$_2$ |
| 3.175 | Br | Br | OCH$_2$CH$_2$ | NEt$_2$ |
| 3.176 | Cl | Br | OCH$_2$CH$_2$ | NEt$_2$ |
| 3.177 | Me | Br | OCH$_2$CH$_2$ | NEt$_2$ |
| 3.178 | Cl | SO$_2$Me | OCH$_2$CH$_2$ | NEt$_2$ |
| 3.179 | Me | SO$_2$Me | OCH$_2$CH$_2$ | NEt$_2$ |
| 3.180 | Cl | SO$_2$Et | OCH$_2$CH$_2$ | NEt$_2$ |
| 3.181 | Cl | Cl | OCH$_2$CH$_2$ | N(n-Pr)$_2$ |
| 3.182 | Br | Br | OCH$_2$CH$_2$ | N(n-Pr)$_2$ |
| 3.183 | Cl | Br | OCH$_2$CH$_2$ | N(n-Pr)$_2$ |
| 3.184 | Me | Br | OCH$_2$CH$_2$ | N(n-Pr)$_2$ |
| 3.185 | Cl | SO$_2$Me | OCH$_2$CH$_2$ | N(n-Pr)$_2$ |
| 3.186 | Me | SO$_2$Me | OCH$_2$CH$_2$ | N(n-Pr)$_2$ |
| 3.187 | Cl | SO$_2$Et | OCH$_2$CH$_2$ | N(n-Pr)$_2$ |
| 3.188 | Cl | Cl | OCH$_2$CH$_2$ | N(i-Pr)$_2$ |
| 3.189 | Me | Br | OCH$_2$CH$_2$ | N(i-Pr)$_2$ |
| 3.190 | Me | NO$_2$ | OCH$_2$CH$_2$ | N(i-Pr)$_2$ |
| 3.191 | NO$_2$ | Cl | OCH$_2$CH$_2$ | N(i-Pr)$_2$ |
| 3.192 | NO$_2$ | Br | OCH$_2$CH$_2$ | N(i-Pr)$_2$ |
| 3.193 | Me | SO$_2$Me | OCH$_2$CH$_2$ | N(i-Pr)$_2$ |
| 3.194 | Cl | SO$_2$Et | OCH$_2$CH$_2$ | N(i-Pr)$_2$ |
| 3.195 | Cl | Cl | OCH$_2$CH$_2$ | NmePh |
| 3.196 | Me | Br | OCH$_2$CH$_2$ | NmePh |
| 3.197 | Me | NO$_2$ | OCH$_2$CH$_2$ | NmePh |
| 3.198 | NO$_2$ | Cl | OCH$_2$CH$_2$ | NmePh |
| 3.199 | NO$_2$ | Br | OCH$_2$CH$_2$ | NmePh |
| 3.200 | Me | SO$_2$Me | OCH$_2$CH$_2$ | NmePh |

TABLE 3-continued

| | | | | |
|---|---|---|---|---|
| 3.201 | Cl | SO₂Et | OCH₂CH₂ | NmePh |
| 3.202 | Cl | Cl | OCH₂CH₂ | -N(pyrrolidinyl) |
| 3.203 | Br | Br | OCH₂CH₂ | -N(pyrrolidinyl) |
| 3.204 | Cl | Br | OCH₂CH₂ | -N(pyrrolidinyl) |
| 3.205 | Me | Br | OCH₂CH₂ | -N(pyrrolidinyl) |
| 3.206 | Cl | SO₂Me | OCH₂CH₂ | -N(pyrrolidinyl) |
| 3.207 | Me | SO₂Me | OCH₂CH₂ | -N(pyrrolidinyl) |
| 3.208 | Cl | SO₂Et | OCH₂CH₂ | -N(pyrrolidinyl) |
| 3.209 | Cl | Cl | OCH₂CH=CH | NMe₂ |
| 3.210 | Cl | SO₂Me | OCH₂CH=CH | NMe₂ |
| 3.211 | Me | Cl | OCH₂CH=CH | NMe₂ |
| 3.212 | Me | Br | OCH₂CH=CH | NMe₂ |
| 3.213 | Me | SO₂Me | OCH₂CH=CH | NMe₂ |
| 3.214 | Cl | Cl | OCH₂CH=CH | NEt₂ |
| 3.215 | Cl | SO₂Me | OCH₂CH=CH | NEt₂ |
| 3.216 | Me | Cl | OCH₂CH=CH | NEt₂ |
| 3.217 | Me | Br | OCH₂CH=CH | NEt₂ |
| 3.218 | Me | SO₂Me | OCH₂CH=CH | NEt₂ |
| 3.219 | Cl | Cl | OCH₂CH=CH | Nh(c-Pr) |
| 3.220 | Cl | SO₂Me | OCH₂CH=CH | Nh(c-Pr) |
| 3.221 | Me | Cl | OCH₂CH=CH | Nh(c-Pr) |
| 3.222 | Me | Br | OCH₂CH=CH | Nh(c-Pr) |
| 3.223 | Me | SO₂Me | OCH₂CH=CH | Nh(c-Pr) |

TABLE 4

Compounds of the formula (I) according to the invention in which the substituents and symbols have the following definitions:

$R^{1c}$ = H   $R^4$ = c-Pr   $R^5$ = Me
$R^6$ = H

| No. | $R^{1a}$ | $R^{1b}$ | X-L | $NR^2R^3$ | Physical data |
|---|---|---|---|---|---|
| 4.1 | Cl | Cl | OCH₂ | NH₂ | |
| 4.2 | Br | Br | OCH₂ | NH₂ | |
| 4.3 | Me | Br | OCH₂ | NH₂ | |
| 4.4 | Cl | SO₂Me | OCH₂ | NH₂ | |
| 4.5 | Cl | SO₂Et | OCH₂ | NH₂ | |
| 4.6 | Me | SO₂Me | OCH₂ | NH₂ | |
| 4.6a | Me | Cl | OCH₂ | NHMe | |
| 4.6b | Me | Br | OCH₂ | NHMe | |
| 4.7 | Cl | Cl | OCH₂ | NHEt | |
| 4.8 | Cl | SO₂Me | OCH₂ | NHEt | |
| 4.8a | Me | Cl | OCH₂ | NHEt | |
| 4.8b | Me | Br | OCH₂ | NHEt | |
| 4.9 | Me | SO₂Me | OCH₂ | NHEt | |
| 4.10 | Br | Br | OCH₂ | NH(i-Pr) | |
| 4.11 | Me | Br | OCH₂ | NH(i-Pr) | |
| 4.12 | Me | NO2 | 00H2 | NH(i-Pr) | |
| 4.13 | Cl | SO₂Et | OCH₂ | NH(i-Pr) | |
| 4.14 | Cl | Cl | OCH₂ | NH(c-Pr) | |
| 4.15 | Cl | Br | OCH₂ | NH(c-Pr) | |
| 4.15a | Me | Cl | OCH₂ | NH(c-Pr) | |
| 4.16 | Me | Br | OCH₂ | NH(c-Pr) | |
| 4.17 | Me | NO2 | OCH₂ | NH(c-Pr) | |
| 4.18 | Cl | SO₂Me | OCH₂ | NH(c-Pr) | |
| 4.19 | Cl | Cl | OCH₂ | NMe₂ | |
| 4.20 | Br | Br | OCH₂ | NMe₂ | |
| 4.20a | Me | Cl | OCH₂ | NMe₂ | $R^f$(EE): 0.04 |
| 4.21 | Cl | Br | OCH₂ | NMe₂ | |
| 4.22 | Me | Br | OCH₂ | NMe₂ | |
| 4.23 | Cl | SO₂Me | OCH₂ | NMe₂ | |
| 4.24 | Me | SO₂Me | OCH₂ | NMe₂ | |
| 4.25 | Cl | SO₂Et | OCH₂ | NMe₂ | |
| 4.26 | Cl | Cl | OCH₂ | NEt₂ | |
| 4.27 | Br | Br | OCH₂ | NEt₂ | |
| 4.27a | Me | Cl | OCH₂ | NEt₂ | $R^f$(EE): 0.06 |
| 4.28 | Cl | Br | OCH₂ | NEt₂ | |
| 4.29 | Me | Br | OCH₂ | NEt₂ | |
| 4.30 | Cl | SO₂Me | OCH₂ | NEt₂ | |
| 4.31 | Me | SO₂Me | OCH₂ | NEt₂ | |
| 4.32 | Cl | SO₂Et | OCH₂ | NEt₂ | |
| 4.33 | Cl | Cl | OCH₂ | N(n-Pr)₂ | |
| 4.34 | Br | Br | OCH₂ | N(n-Pr)₂ | |
| 4.35 | Cl | Br | OCH₂ | N(n-Pr)₂ | |
| 4.36 | Me | Br | OCH₂ | N(n-Pr)₂ | |
| 4.37 | Cl | SO₂Me | OCH₂ | N(n-Pr)₂ | |
| 4.38 | Me | SO₂Me | OCH₂ | N(n-Pr)₂ | |
| 4.39 | Cl | SO₂Et | OCH₂ | N(n-Pr)₂ | |
| 4.40 | Cl | Cl | OCH₂ | N(i-Pr)₂ | |
| 4.41 | Me | Br | OCH₂ | N(i-Pr)₂ | |
| 4.42 | Me | NO₂ | OCH₂ | N(i-Pr)₂ | |
| 4.43 | NO2 | Cl | OCH₂ | N(i-Pr)₂ | |
| 4.44 | NO2 | Br | OCH₂ | N(i-Pr)₂ | |
| 4.45 | Me | SO₂Me | OCH₂ | N(i-Pr)₂ | |
| 4.46 | Cl | SO₂Et | OCH₂ | N(i-Pr)₂ | |
| 4.47 | Cl | Cl | OCH₂ | NmePh | |
| 4.48 | Me | Br | OCH₂ | NmePh | |
| 4.49 | Me | NO₂ | OCH₂ | NmePh | |
| 4.50 | NO₂ | Cl | OCH₂ | NmePh | |
| 4.51 | NO₂ | Br | OCH₂ | NmePh | |
| 4.52 | Me | SO₂Me | OCH₂ | NmePh | |
| 4.53 | Cl | SO₂Et | OCH₂ | NmePh | |
| 4.54 | Cl | Cl | OCH₂ | -N(pyrrolidinyl) | |
| 4.55 | Br | Br | OCH₂ | -N(pyrrolidinyl) | |
| 4.56 | Cl | Br | OCH₂ | -N(pyrrolidinyl) | |
| 4.57 | Me | Br | OCH₂ | -N(pyrrolidinyl) | |
| 4.58 | Cl | SO₂Me | OCH₂ | -N(pyrrolidinyl) | |
| 4.59 | Me | SO₂Me | OCH₂ | -N(pyrrolidinyl) | |

TABLE 4-continued

| | | | | |
|---|---|---|---|---|
| 4.60 | Cl | SO₂Et | OCH₂ | 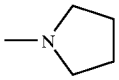 |
| 4.61 | Cl | Cl | OCH₂ | 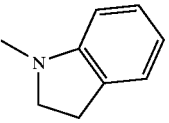 |
| 4.62 | Br | Br | OCH₂ | 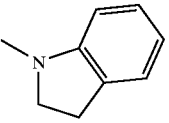 |
| 4.63 | Cl | Br | OCH₂ | 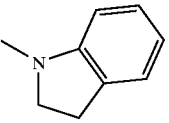 |
| 4.64 | Me | Br | OCH₂ | 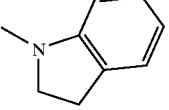 |
| 4.65 | Cl | SO₂Me | OCH₂ | 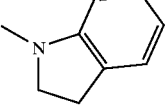 |
| 4.66 | Me | SO₂Me | OCH₂ | 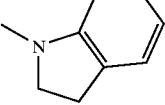 |
| 4.67 | Cl | SO₂Et | OCH₂ | 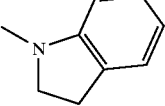 |
| 4.68 | Cl | Cl | OCH₂ |  |
| 4.69 | Me | Br | OCH₂ | 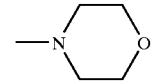 |
| 4.70 | Me | NO₂ | OCH₂ |  |
| 4.71 | NO₂ | Cl | OCH₂ | 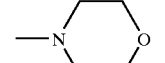 |
| 4.72 | NO₂ | Br | OCH₂ | 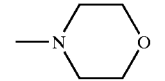 |

TABLE 4-continued

| | | | | | |
|---|---|---|---|---|---|
| 4.73 | Me | SO₂Me | OCH₂ | 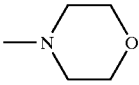 | |
| 4.74 | Cl | SO₂Et | OCH₂ |  | |
| 4.75 | Cl | Cl | OCH(Me) | NH₂ | |
| 4.76 | Br | Br | OCH(Me) | NH₂ | |
| 4.77 | Me | Br | OCH(Me) | NH₂ | |
| 4.78 | Cl | SO₂Me | OCH(Me) | NH₂ | |
| 4.79 | Cl | SO₂Et | OCH(Me) | NH₂ | |
| 4.80 | Me | SO₂Me | OCH(Me) | NH₂ | |
| 4.80a | Cl | Cl | OCH(Me) | NHMe | |
| 4.80b | Cl | SO₂Me | OCH(Me) | NHMe | |
| 4.80c | Me | Cl | OCH(Me) | NHMe | |
| 4.80d | Me | Br | OCH(Me) | NHMe | |
| 4.80e | Me | SO₂Me | OCH(Me) | NHMe | |
| 4.81 | Cl | Cl | OCH(Me) | NHEt | |
| 4.82 | Cl | SO₂Me | OCH(Me) | NHEt | |
| 4.82a | Me | Cl | OCH(Me) | NHEt | |
| 4.82b | Me | Br | OCH(Me) | NH(Allyl) | |
| 4.82c | Cl | Cl | OCH(Me) | NH(Allyl) | |
| 4.82d | Cl | SO₂Me | OCH(Me) | NH(Allyl) | |
| 4.82e | Me | Cl | OCH(Me) | NH(Allyl) | |
| 4.82f | Me | Br | OCH(Me) | NH(Allyl) | |
| 4.82g | Me | SO₂Me | OCH(Me) | NH(Allyl) | |
| 4.83 | Me | SO₂Me | OCH(Me) | NHEt | |
| 4.84 | Br | Br | OCH(Me) | NH(i-Pr) | |
| 4.85 | Me | Br | OCH(Me) | NH(i-Pr) | |
| 4.86 | Me | NO₂ | OCH(Me) | NH(i-Pr) | |
| 4.87 | Cl | SO₂Et | OCH(Me) | NH(i-Pr) | |
| 4.88 | Cl | Cl | OCH(Me) | NH(c-Pr) | |
| 4.89 | Cl | Br | OCH(Me) | NH(c-Pr) | |
| 4.90 | Me | Br | OCH(Me) | NH(c-Pr) | |
| 4.91 | Me | NO₂ | OCH(Me) | NH(c-Pr) | |
| 4.92 | Cl | SO₂Me | OCH(Me) | NH(c-Pr) | |
| 4.93 | Cl | Cl | OCH(Me) | NMe₂ | |
| 4.94 | Br | Br | OCH(Me) | NMe₂ | |
| 4.95 | Cl | Br | OCH(Me) | NMe₂ | |
| 4.96 | Me | Br | OCH(Me) | NMe₂ | R$^f$(EE): 0.01 |
| 4.97 | Cl | SO₂Me | OCH(Me) | NMe₂ | |
| 4.98 | Me | SO₂Me | OCH(Me) | NMe₂ | |
| 4.99 | Cl | SO₂Et | OCH(Me) | NMe₂ | |
| 4.100 | Cl | Cl | OCH(Me) | NEt₂ | |
| 4.101 | Br | Br | OCH(Me) | NEt₂ | |
| 4.102 | Cl | Br | OCH(Me) | NEt₂ | |
| 4.103 | Me | Br | OCH(Me) | NEt₂ | |
| 4.104 | Cl | SO₂Me | OCH(Me) | NEt₂ | |
| 4.105 | Me | SO₂Me | OCH(Me) | NEt₂ | |
| 4.106 | Cl | SO₂Et | OCH(Me) | NEt₂ | |
| 4.107 | Cl | Cl | OCH(Me) | N(n-Pr)₂ | |
| 4.108 | Br | Br | OCH(Me) | N(n-Pr)₂ | |
| 4.109 | Cl | Br | OCH(Me) | N(n-Pr)₂ | |
| 4.110 | Me | Br | OCH(Me) | N(n-Pr)₂ | |
| 4.111 | Cl | SO₂Me | OCH(Me) | N(n-Pr)₂ | |
| 4.112 | Me | SO₂Me | OCH(Me) | N(n-Pr)₂ | |
| 4.113 | Cl | SO₂Et | OCH(Me) | N(n-Pr)₂ | |
| 4.114 | Cl | Cl | OCH(Me) | N(i-Pr)₂ | |
| 4.115 | Me | Br | OCH(Me) | N(i-Pr)₂ | |
| 4.116 | Me | NO₂ | OCH(Me) | N(i-Pr)₂ | |
| 4.117 | NO₂ | Cl | OCH(Me) | N(i-Pr)₂ | |
| 4.118 | NO₂ | Br | OCH(Me) | N(i-Pr)₂ | |
| 4.119 | Me | SO₂Me | OCH(Me) | N(i-Pr)₂ | |
| 4.120 | Cl | SO₂Et | OCH(Me) | N(i-Pr)₂ | |
| 4.121 | Cl | Cl | OCH(Me) | NmePh | |
| 4.122 | Me | Br | OCH(Me) | NmePh | |
| 4.123 | Me | NO₂ | OCH(Me) | NmePh | |
| 4.124 | NO₂ | Cl | OCH(Me) | NmePh | |
| 4.125 | NO₂ | Br | OCH(Me) | NmePh | |
| 4.126 | Me | SO₂Me | OCH(Me) | NmePh | |
| 4.127 | Cl | SO₂Et | OCH(Me) | NmePh | |

TABLE 4-continued

| | | | | |
|---|---|---|---|---|
| 4.128 | Cl | Cl | OCH(Me) | 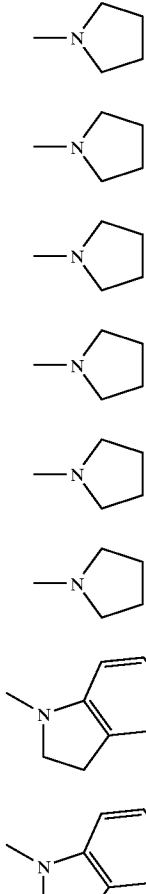 pyrrolidine |
| 4.129 | Br | Br | OCH(Me) | pyrrolidine |
| 4.130 | Cl | Br | OCH(Me) | pyrrolidine |
| 4.131 | Me | Br | OCH(Me) | pyrrolidine |
| 4.132 | Cl | SO₂Me | OCH(Me) | pyrrolidine |
| 4.133 | Me | SO₂Me | OCH(Me) | pyrrolidine |
| 4.134 | Cl | SO₂Et | OCH(Me) | pyrrolidine |
| 4.135 | Cl | Cl | OCH(Me) | 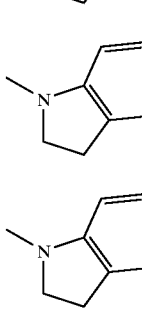 indoline |
| 4.136 | Br | Br | OCH(Me) | indoline |
| 4.137 | Cl | Br | OCH(Me) | indoline |
| 4.138 | Me | Br | OCH(Me) | indoline |
| 4.139 | Cl | SO₂Me | OCH(Me) | indoline |
| 4.140 | Me | SO₂Me | OCH(Me) | indoline |

TABLE 4-continued

| | | | | |
|---|---|---|---|---|
| 4.141 | Cl | SO₂Et | OCH(Me) | 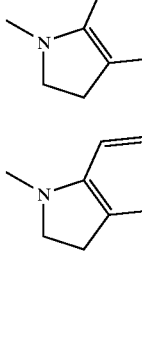 indoline |
| 4.142 | Cl | Cl | OCH(Me) |  morpholine |
| 4.143 | Me | Br | OCH(Me) | morpholine |
| 4.144 | Me | NO₂ | OCH(Me) | morpholine |
| 4.145 | NO₂ | Cl | OCH(Me) | morpholine |
| 4.146 | NO₂ | Br | OCH(Me) | morpholine |
| 4.147 | Me | SO₂Me | OCH(Me) | morpholine |
| 4.148 | Cl | SO₂Et | OCH(Me) | morpholine |
| 4.149 | Cl | Cl | OCH₂CH₂ | NH₂ |
| 4.150 | Br | Br | OCH₂CH₂ | NH₂ |
| 4.151 | Me | Br | OCH₂CH₂ | NH₂ |
| 4.152 | Cl | SO₂Me | OCH₂CH₂ | NH₂ |
| 4.153 | Cl | SO₂Et | OCH₂CH₂ | NH₂ |
| 4.154 | Me | SO₂Me | OCH₂CH₂ | NH₂ |
| 4.155 | Cl | Cl | OCH₂CH₂ | NHEt |
| 4.156 | Cl | SO₂Me | OCH₂CH₂ | NHEt |
| 4.157 | Me | SO₂Me | OCH₂CH₂ | NHEt |
| 4.158 | Br | Br | OCH₂CH₂ | NH(i-Pr) |
| 4.159 | Me | Br | OCH₂CH₂ | NH(i-Pr) |
| 4.160 | Me | NO₂ | OCH₂CH₂ | NH(i-Pr) |
| 4.161 | Cl | SO₂Et | OCH₂CH₂ | NH(i-Pr) |
| 4.162 | Cl | Cl | OCH₂CH₂ | NH(c-Pr) |
| 4.163 | Cl | Br | OCH₂CH₂ | NH(c-Pr) |
| 4.164 | Me | Br | OCH₂CH₂ | NH(c-Pr) |
| 4.165 | Me | NO₂ | OCH₂CH₂ | NH(c-Pr) |
| 4.166 | Cl | SO₂Me | OCH₂CH₂ | NH(c-Pr) |
| 4.167 | Cl | Cl | OCH₂CH₂ | NMe₂ |
| 4.168 | Br | Br | OCH₂CH₂ | NMe₂ |
| 4.169 | Cl | Br | OCH₂CH₂ | NMe₂ |
| 4.170 | Me | Br | OCH₂CH₂ | NMe₂ |
| 4.171 | Cl | SO₂Me | OCH₂CH₂ | NMe₂ |
| 4.172 | Me | SO₂Me | OCH₂CH₂ | NMe₂ |
| 4.173 | Cl | SO₂Et | OCH₂CH₂ | NMe₂ |
| 4.174 | Cl | Cl | OCH₂CH₂ | NEt₂ |
| 4.175 | Br | Br | OCH₂CH₂ | NEt₂ |
| 4.176 | Cl | Br | OCH₂CH₂ | NEt₂ |
| 4.177 | Me | Br | OCH₂CH₂ | NEt₂ |
| 4.178 | Cl | SO₂Me | OCH₂CH₂ | NEt₂ |
| 4.179 | Me | SO₂Me | OCH₂CH₂ | NEt₂ |
| 4.180 | Cl | SO₂Et | OCH₂CH₂ | NEt₂ |
| 4.181 | Cl | Cl | OCH₂CH₂ | N(n-Pr)₂ |
| 4.182 | Br | Br | OCH₂CH₂ | N(n-Pr)₂ |
| 4.183 | Cl | Br | OCH₂CH₂ | N(n-Pr)₂ |
| 4.184 | Me | Br | OCH₂CH₂ | N(n-Pr)₂ |
| 4.185 | Cl | SO₂Me | OCH₂CH₂ | N(n-Pr)₂ |
| 4.186 | Me | SO₂Me | OCH₂CH₂ | N(n-Pr)₂ |

TABLE 4-continued

| No. | | | | |
|---|---|---|---|---|
| 4.187 | Cl | SO$_2$Et | OCH$_2$CH$_2$ | N(n-Pr)$_2$ |
| 4.188 | Cl | Cl | OCH$_2$CH$_2$ | N(i-Pr)$_2$ |
| 4.189 | Me | Br | OCH$_2$CH$_2$ | N(i-Pr)$_2$ |
| 4.190 | Me | NO$_2$ | OCH$_2$CH$_2$ | N(i-Pr)$_2$ |
| 4.191 | NO$_2$ | Cl | OCH$_2$CH$_2$ | N(i-Pr)$_2$ |
| 4.192 | NO$_2$ | Br | OCH$_2$CH$_2$ | N(i-Pr)$_2$ |
| 4.193 | Me | SO$_2$Me | OCH$_2$CH$_2$ | N(i-Pr)$_2$ |
| 4.194 | Cl | SO$_2$Et | OCH$_2$CH$_2$ | N(i-Pr)$_2$ |
| 4.195 | Cl | Cl | OCH$_2$CH$_2$ | NmePh |
| 4.196 | Me | Br | OCH$_2$CH$_2$ | NmePh |
| 4.197 | Me | NO$_2$ | OCH$_2$CH$_2$ | NmePh |
| 4.198 | NO$_2$ | Cl | OCH$_2$CH$_2$ | NmePh |
| 4.199 | NO$_2$ | Br | OCH$_2$CH$_2$ | NmePh |
| 4.200 | Me | SO$_2$Me | OCH$_2$CH$_2$ | NmePh |
| 4.201 | Cl | SO$_2$Et | OCH$_2$CH$_2$ | NmePh |
| 4.202 | Cl | Cl | OCH$_2$CH$_2$ | 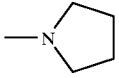 |
| 4.203 | Br | Br | OCH$_2$CH$_2$ | 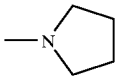 |
| 4.204 | Cl | Br | OCH$_2$CH$_2$ | 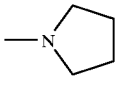 |
| 4.205 | Me | Br | OCH$_2$CH$_2$ | 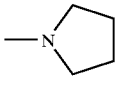 |
| 4.206 | Cl | SO$_2$Me | OCH$_2$CH$_2$ | 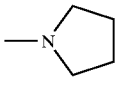 |
| 4.207 | Me | SO$_2$Me | OCH$_2$CH$_2$ | 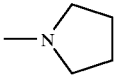 |
| 4.208 | Cl | SO$_2$Et | OCH$_2$CH$_2$ | 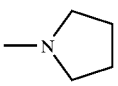 |
| 4.209 | Cl | Cl | OCH$_2$CH=CH | NMe$_2$ |
| 4.210 | Cl | SO$_2$Me | OCH$_2$CH=CH | NMe$_2$ |
| 4.211 | Me | Cl | OCH$_2$CH=CH | NMe$_2$ |
| 4.212 | Me | Br | OCH$_2$CH=CH | NMe$_2$ |
| 4.213 | Me | SO$_2$Me | OCH$_2$CH=CH | NMe$_2$ |
| 4.214 | Cl | Cl | OCH$_2$CH=CH | NEt$_2$ |
| 4.215 | Cl | SO$_2$Me | OCH$_2$CH=CH | NEt$_2$ |
| 4.216 | Me | Cl | OCH$_2$CH=CH | NEt$_2$ |
| 4.217 | Me | Br | OCH$_2$CH=CH | NEt$_2$ |
| 4.218 | Me | SO$_2$Me | OCH$_2$CH=CH | NEt$_2$ |
| 4.219 | Cl | Cl | OCH$_2$CH=CH | Nh(c-Pr) |
| 4.220 | Cl | SO$_2$Me | OCH$_2$CH=CH | Nh(c-Pr) |
| 4.221 | Me | Cl | OCH$_2$CH=CH | Nh(c-Pr) |
| 4.222 | Me | Br | OCH$_2$CH=CH | Nh(c-Pr) |
| 4.223 | Me | SO$_2$Me | OCH$_2$CH=CH | Nh(c-Pr) |

TABLE 5

Compounds of the formula (I) according to the invention in which the substituents and symbols have the following definitions:

$R^{1c}$ = H   $R^4$ = Me   $R^6$ = c-Pr
$Y$ = O

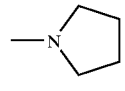

| No. | $R^{1a}$ | $R^{b}$ | $R^4$ | $R^5$ | $R^5$ | X-L | NR$^2$R$^3$ | Physical data |
|---|---|---|---|---|---|---|---|---|
| 5.1 | Cl | Cl | H | Me | Bz | OCH$_2$ | NEt$_2$ | |
| 5.2 | Cl | SO$_2$Et | H | Me | SO$_2$-(n-Pr) | OCH$_2$ |  | |
| 5.3 | Me | Br | H | Me | CH$_2$-(2,6-F$_2$-Ph) | OCH$_2$ | NMe$_2$ | |
| 5.4 | Cl | Cl | H | Me | CH$_2$-Bz | OCH$_2$ | NH(c-Pr) | |
| 5.5 | Cl | Cl | H | Et | Bz | OCH$_2$ | NEt$_2$ | |

TABLE 5-continued

| | | | | | | | |
|---|---|---|---|---|---|---|---|
| 5.6 | Cl | SO₂Et | H | Et | SO₂-(n-Pr) | OCH₂ | 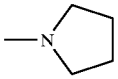 |
| 5.7 | Me | Br | H | Et | CH₂-(2,6-F₂-Ph) | OCH₂ | NMe₂ |
| 5.8 | Cl | Cl | H | Et | CH₂-Bz | OCH₂ | NH(c-Pr) |
| 5.9 | Cl | Cl | Me | Me | Bz | OCH₂ | NEt₂ |
| 5.10 | Cl | SO₂Et | Me | Me | SO₂-(n-Pr) | OCH₂ | 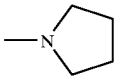 |
| 5.11 | Me | Br | Me | Me | CH₂-(2,6-F₂-Ph) | OCH₂ | NMe₂ |
| 5.12 | Cl | Cl | Me | Me | CH₂-Bz | OCH₂ | NH(c-Pr) |
| 5.13 | Cl | Cl | H | Me | Bz | OC(Me)H | NEt₂ |
| 5.14 | Cl | SO₂Et | H | Me | SO₂-(n-Pr) | OC(Me)H | 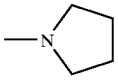 |
| 5.15 | Me | Br | H | Me | CH₂-(2,6-F₂-Ph) | OC(Me)H | NMe₂ |
| 5.16 | Cl | Cl | H | Me | CH₂-Bz | OC(Me)H | NH(c-Pr) |
| 5.17 | Cl | Cl | H | Et | Bz | OC(Me)H | NEt₂ |
| 5.18 | Cl | SO₂Et | H | Et | SO₂-(n-Pr) | OC(Me)H | 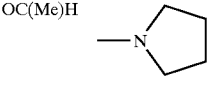 |
| 5.19 | Me | Br | H | Et | CH₂-(2,6-F₂-Ph) | OC(Me)H | NMe₂ |
| 5.20 | Cl | Cl | H | Et | CH₂-Bz | OC(Me)H | NH(c-Pr) |
| 5.21 | Cl | Cl | Me | Me | Bz | OC(Me)H | NEt₂ |
| 5.22 | Cl | SO₂Et | Me | Me | SO₂-(n-Pr) | OC(Me)H | 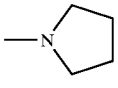 |
| 5.23 | Me | Br | Me | Me | CH₂-(2,6-F₂-Ph) | OC(Me)H | NMe₂ |
| 5.24 | Cl | Cl | Me | Me | CH₂-Bz | OC(Me)H | NH(c-Pr) |

B. Formulation Examples

1. Dust
A dust is obtained by mixing 10 parts by weight of a compound of the formula (I) and 90 parts by weight of talc as inert substance and comminuting the mixture in a hammer mill.

2. Dispersible Powder
A wettable powder which is readily dispersible in water is obtained by mixing 25 parts by weight of a compound of the formula (I), 64 parts by weight of kaolin-containing quartz as inert material, 10 parts by weight of potassium ligninsulfonate and 1 part by weight of sodium oleoylmethyltauride as wetter and dispersant, and grinding the mixture in a pinned-disk mill.

3. Dispersion Concentrate
A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate
An emulsifiable concentrate is obtained from 15 parts by weight of the compound of the formula (I), 75 parts by weight of cyclohexanone as solvent and 10 parts by weight of oxethylated nonylphenol as emulsifier.

5. Water-Dispersible Granules
Water-dispersible granules are obtained by mixing 75 parts by weight of a compound of the formula (I),
10" calcium ligninsulfonate,
5" sodium lauryl sulfate,
3" polyvinyl alcohol and
7" kaolin,
grinding the mixture in a pinned-disk mill and granulating the powder in a fluidized bed by spraying on water as granulation liquid.

Water-dispersible granules are also obtained by homogenizing and precomminuting, in a colloid mill, 25 parts by weight of a compound of the formula (I),
5" sodium 2,2'-dinaphthylmethane-6,6'-disulfonate,
2" sodium oleoylmethyltauride,
1" polyvinyl alcohol,
17" calcium carbonate and
50" water,
subsequently grinding the mixture in a bead mill, and atomizing and drying the resulting suspension in a spray tower by means of a single-substance nozzle.

C. Biological Examples

1. Post-Emergence Herbicidal Action Against Weed Plants

Seeds of mono- and dicotyledonous weed plants are placed in sandy loam in cardboard pots, covered with soil and grown in the greenhouse under good growth conditions. 2 to 3 weeks after sowing, the test plants are treated at the three-leaf stage. The compounds according to the invention, which are formulated as wettable powders or as emulsion concentrates, are sprayed at a dosage as given in tables 1 to 5 onto the surface of the green plant parts at an application rate of 600 to 800 l of water per ha (converted). After the test plants have been left to stand in the greenhouse for 3 to 4 weeks under optimal growth conditions, the effect of the compounds is scored visually in comparison to the prior art compounds. As the results of the comparison tables show, the chosen compounds according to the invention have an outstanding activity against a broad spectrum of economically important monocotyledonous and dicotyledonous weed plants.

2. Crop Plant Tolerance

In further greenhouse experiments, seeds of barley weed and of monocotyledonous and dicotyledonous harmful plants are placed in sandy loam, covered with soil and placed in the greenhouse until the plants have developed two to three true leaves. Then they are treated with the compounds of the formula (I) according to the invention and, for comparison, with those of the prior art, as described above in section 1. Four to five weeks after the application and after having been left to stand in the greenhouse, visual scoring reveals that the compounds according to the invention are outstandingly well tolerated by important crop plants, in particular wheat, maize and rice.

What is claimed is:

1. A compound of the formula (I) or salt thereof

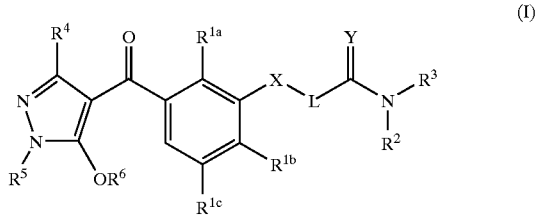

(I)

in which the radical and the indices have the following definitions:

X is O;

L is CH;

Y is oxygen;

$R^{1a}, R^{1b}, R^{1c}$ independently are each hydrogen, mercapto, nitro, halogen, cyano, thiocyanato, $(C_1-C_6)$-alkyl-CO—O, $(C_1-C_6)$-alkyl-S(O)$_n$—O, $(C_1-C_6)$-alkyl-S(O)$_m$, $(C_1-C_6)$-haloalkyl-S(O)$_m$, $(C_3-C_7)$-cycloalkyl-S(O)$_m$, di-$(C_1-C_6)$-alkyl-N—SO$_2$, $(C_1-C_6)$-alkyl-SO$_2$—NH, $(C_1-C_6)$-alkyl-NH—CO, di-$(C_1-C_6)$-alkyl-N—CO, $(C_1-C_6)$-alkyl-SO$_2$—[$(C_1-C_6)$-alkyl]amino, $(C_1-C_6)$-alkyl-CO—[$(C_1-C_6)$-alkyl]amino, $(C_1-C_6)$-alkyl-O—CH$_2$, $(C_1-C_6)$-alkyl-S(O)$_n$—CH$_2$, $(C_1-C_6)$-alkyl-NH—CH$_2$, or are each $(C_1-C_6)$-alkyl-(Y)$_p$, $(C_2-C_6)$-alkenyl-(Y)$_p$, $(C_2-C_6)$-alkynyl-(Y)$_p$, $(C_3-C_9)$-cycloalkyl-(Y)$_p$, $(C_3-C_9)$-cycloalkenyl-(Y)$_p$, $(C_1-C_6)$-alkyl-$(C_3-C_9)$-cycloalkyl-(Y)$_p$ or $(C_1-C_6)$-alkyl-$(C_3-C_9)$-cycloalkenyl-(Y)$_p$ each of which is substituted by v radicals from the group consisting of cyano, nitro and halogen;

$R^2$ and $R^3$ together with the nitrogen atom linking them form a pyyrole ring;

$R^4$ is hydrogen, $(C_1-C_6)$-alkyl or $(C_1-C_6)$-haloalkyl, $(C_3-C_9)$-cycloalkyl or $(C_3-C_9)$-halocycloalkyl;

$R^5$ is $(C_1-C_6)$-alkyl, halo-$(C_1-C_6)$-alkyl, $(C_3-C_9)$-cycloalkyl, $(C_3-C_9)$-halo-cycloalkyl, or is phenyl substituted by v radicals from the group consisting of halogen, nitro, cyano, $(C_1-C_4)$-alkyl, halo-$(C_1-C_4)$-alkyl, $(C_1-C_4)$-alkoxy and halo-$(C_1-C_4)$-alkoxy;

$R^6$ is hydrogen, $(C_1-C_6)$-alkyl, halo-$(C_1-C_6)$-alkyl, $(C_1-C_6)$-alkylcarbonyl, halo-$(C_1-C_6)$-alkylcarbonyl, $(C_1-C_6)$-alkoxycarbonyl, halo-$(C_1-C_6)$-alkoxycarbonyl, $(C_1-C_6)$-alkylaminocarbonyl, halo-$(C_1-C_6)$-alkylaminocarbonyl, $(C_1-C_6)$-dialkylaminocarbonyl, halo-$(C_1-C_6)$-dialkylaminocarbonyl, $(C_1-C_6)$-alkylsulfonyl, halo-$(C_1-C_6)$-alkylsulfonyl, or is benzyl, benzoyl, benzoylmethyl, phenoxycarbonyl or phenylsulfonyl each of which is substituted by v radicals from the group consisting of halogen, nitro, cyano, $(C_1-C_4)$-alkyl, halo-$(C_1-C_4)$-alkyl, $(C_1-C_4)$-alkoxy and halo-$(C_1-C_4)$-alkoxy;

| m | is 1 or 2; |
|---|---|
| n | is 0, 1 or 2; |
| p | is 0 or 1; |
| v | is 0, 1, 2 or 3; |
| w and x | independently are each 0, 1, 2, 3 or 4; |
| | w and x should not both be zero at the same time. |

2. A compound as claimed in claim 1, wherein $R^{1c}$ is hydrogen.

3. A compound as claimed in claim 1, wherein $R^{1a}, R^{1b}$ independently are each F, Cl, Br, $CH_3$, $CH_3S$, $CH_3O$, $CH_3SO_2$, $C_2H_5SO_2$, $CF_3CH_2SO_2$, cyclopropyl-$SO_2$, $CF_3$ or $NO_2$.

4. A compound as claimed in claim 1, wherein $R^4$ is hydrogen, methyl or cyclopropyl.

5. A compound as claimed in claim 1, wherein $R^6$ is hydrogen, $(C_1-C_6)$-alkyl, $(C_1-C_6)$-alkylcarbonyl, $(C_1-C_6)$-alkylsulfonyl, or is benzoyl or phenylsulfonyl each of which is substituted by v radicals from the group consisting of halogen, nitro, cyano, $(C_1-C_4)$-alkyl, halo-$(C_1-C_4)$-alkyl, $(C_1-C_4)$-alkoxy and halo-$(C_1-C_4)$-alkoxy.

6. A compound as claimed in claim 1, wherein $R^{1a}, R^{1b}$ independently are each Cl, Br, $NO_2$, $CH_3$, $CH_3SO_2$ or $C_2H_5SO_2$; and $R^5$ is methyl or ethyl.

7. A herbicidal composition comprising a herbicidally effective amount of at least one compound of the general formula (I) as claimed in claim 1.

8. A herbicidal composition as claimed in claim 7 in a mixture with formulating auxiliaries.

9. A method of controlling unwanted plants, which comprises applying an effective amount of at least one compound of the general formula (I) as claimed in claim 1 to the plants or to the site of the unwanted plant growth.

10. The use as claimed in claim 9, wherein the unwanted plants in crops of useful plants.

11. The use as claimed in claim 10, wherein the useful plants are transgenic.

12. A method of controlling unwanted plants, which comprises applying the herbicidal composition as claimed in claim 7 to the plants or to the site of the unwanted plant growth.

13. A method of controlling unwanted plants, which comprises applying the herbicidal composition as claimed in claim 8 to the plants or to the site of the unwanted plant growth.

* * * * *

UNITED STATES PATENT AND TRADEMARK OFFICE
CERTIFICATE OF CORRECTION

PATENT NO. : 6,894,070 B2 Page 1 of 1
DATED : May 17, 2005
INVENTOR(S) : Seitz et al.

It is certified that error appears in the above-identified patent and that said Letters Patent is hereby corrected as shown below:

<u>Column 47,</u>
Line 45, "L is CH;" should read -- L is $CH_2$ --.
Line 65, "form a pyyrole ring;" should read -- form a pyrrole ring; --.

<u>Column 48,</u>
Line 54, "The use as claimed in claim 9, wherein the unwanted" should read -- The method as claimed in claim 9, wherein the unwanted --.
Line 56, "The use as claimed in claim 10, wherein the useful" should read -- The method as claimed in claim 10, wherein the useful --.

Signed and Sealed this

Second Day of May, 2006

JON W. DUDAS
*Director of the United States Patent and Trademark Office*